United States Patent [19]

Roth

[11] Patent Number: 4,681,893

[45] Date of Patent: Jul. 21, 1987

[54] TRANS-6-[2-(3- OR 4-CARBOXAMIDO-SUBSTITUTED PYRROL-1-YL)ALKYL]-4-HYDROXYPYRAN-2-ONE INHIBITORS OF CHOLESTEROL SYNTHESIS

[75] Inventor: Bruce D. Roth, Ann Arbor, Mich.

[73] Assignee: Warner-Lambert Company, Morris Plains, N.J.

[21] Appl. No.: 868,867

[22] Filed: May 30, 1986

[51] Int. Cl.[4] .................... A61K 31/40; A61K 31/35; C07D 207/327

[52] U.S. Cl. .................................. 514/422; 514/423; 546/256; 546/275; 548/517; 548/537

[58] Field of Search ............... 548/517, 537; 514/422, 514/423

[56] References Cited

U.S. PATENT DOCUMENTS

| | | | |
|---|---|---|---|
| 3,983,140 | 9/1976 | Endo et al. | 549/292 |
| 4,049,495 | 9/1977 | Endo et al. | 435/125 |
| 4,137,322 | 1/1979 | Endo et al. | 548/344 X |
| 4,198,425 | 4/1980 | Mitsui et al. | 514/460 |
| 4,255,444 | 3/1981 | Oka et al. | 549/292 X |
| 4,262,013 | 4/1981 | Mitsui et al. | 549/292 X |
| 4,375,475 | 3/1983 | Willard et al. | 514/460 |

OTHER PUBLICATIONS

Singer, et al.; Proc. Soc. Exper. Biol. Med.; vol. 102, pp. 370–373, (1959).
Hulcher; Arch. Biochem. Biophys., vol. 146, pp. 422–427, (1971).
Brown, et al.; New England Jour. of Med., vol. 305, No. 9, pp. 515–517, (1981).
Brown, et al.; J. Chem. Soc. Perkin I, (1976), pp. 1165–1170.
Journal of the Americas Medical Assoc.; (1984), vol. 251, pp. 351–364, 365–374.

Primary Examiner—Joseph Paul Brust
Attorney, Agent, or Firm—Jerry F. Janssen

[57] ABSTRACT

Certain trans-6-[2-(3- or 4-carboxamido-substituted pyrrol-1-yl)alkyl]-4-hydroxypyran-2-ones and the corresponding ring-opened acids derived therefrom which are potent inhibitors of the enzyme 3-hydroxy-3-methylglutaryl-coenzyme A reductase (HMG CoA reductase and are thus useful hypolipidemic or hypocholesterolemic agents. Pharmaceutical compositions containing such compounds, and a method of inhibiting the biosynthesis of cholesterol employing such pharmaceutical compositions are also disclosed.

9 Claims, No Drawings

TRANS-6-[2-(3- OR 4-CARBOXAMIDO-SUBSTITUTED PYRROL-1-YL)ALKYL]-4-HYDROXYPYRAN-2-ONE INHIBITORS OF CHOLESTEROL SYNTHESIS

BACKGROUND OF THE INVENTION

The present invention is related to compounds and pharmaceutical compositions useful as hypocholesterolemic and hypolipidemic agents. More particularly, this invention concerns certain trans-6-[2-(3- or 4-carboxamidosubstitutedpyrrol-1-yl)alkyl]-4-hydroxypyran-2-ones and the corresponding ring-opened acids derived therefrom which are potent inhibitors of the enzyme 3-hydroxy-3-methylglutaryl-coenzyme A reductase (HMG CoA reductase), pharmaceutical compositions containing such compounds, and a method of inhibiting the biosynthesis of cholesterol employing such pharmaceutical compositions.

High levels of blood cholesterol and blood lipids are conditions involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine,* 305, No. 9, 515–517 (1981). It has now been established that lowering LDL-C levels affords protection from coronary heart disease (cf. *Journal of the American Medical Association,* 251, No. 3, 351–374 (1984).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer et al., *Proc. Soc. Exper. Biol. Med.,* 102: 370 (1959) and F. H. Hulcher, *Arch. Biochem. Biophys.,* 146: 422 (1971)).

U.S. Pat. Nos. 3,983,140; 4,049,495 and 4,137,322 disclose the fermentative production of a natural product, now called compactin, having an inhibitory effect on cholesterol biosynthesis. Compactin has been shown to have a complex structure which includes a mevalonolactone moiety (Brown et al., *J. Chem. Soc. Perkin* I (1976) 1165.

U.S. Pat. No. 4,255,444 to Oka et al. discloses several synthetic derivatives of mevalonolactone having antilipidemic activity.

U.S. Pat. Nos. 4,198,425 and 4,262,013 to Mitsue et al. disclose aralkyl derivatives of mevalonolactone which are useful in the treatment of hyperlipidemia.

U.S. Pat. no. 4,375,475 to Willard et al. discloses certain substituted 4-hydroxytetrahydropyran-2-ones which, in the 4(R)-trans-stereoisomeric form, are inhibitors of cholesterol biosynthesis.

Published PCT application No. WO 84/01231 discloses certain indole analogs and derivatives of mevalonolactone having utility as hypolipoproteinemic and antiatherosclerotic agents.

SUMMARY OF THE INVENTION

In accordance with the present invention, there are provided certain trans-6-[2-(3- or 4-carboxamido-substituted pyrrol-1-yl)alkyl]-4-hydroxypyran-2-ones and the corresponding ring-opened hydroxy-acids derived therefrom which are potent inhibitors of cholesterol biosynthesis by virtue of their ability to inhibit the enzyme 3-hydroxy-3-methylglutaryl coenzyme A reductase (HMG-CoA reductase).

In particular, in its broadest aspect the present invention provides compounds of structural formula I

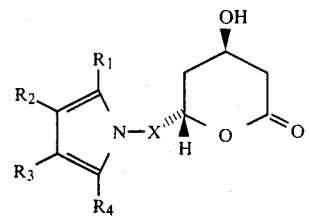

wherein X is —CH$_2$—, —CH$_2$CH$_2$—, —CH$_2$CH$_2$CH$_2$— or —CH$_2$CH(CH$_3$)—.

R$_1$ is 1-naphthyl; 2-naphthyl; cyclohexyl; norbornenyl; 2-, 3-, or 4-pyridinyl; phenyl, phenyl substituted with fluorine, chlorine, bromine, hydroxyl; trifluoromethyl; alkyl of from one to four carbon atoms, alkoxy of from one to four carbon atoms, or alkanoyloxy of from two to eight carbon atoms.

Either R$_2$ or R$_3$ is —CONR$_5$R$_6$ where R$_5$ and R$_6$ are independently hydrogen; alkyl of from one to six carbon atoms; 2-, 3-, or 4-pyridinyl; phenyl; phenyl substituted with fluorine, chlorine, bromine, cyano, trifluoromethyl, or carboalkoxy of from three to eight carbon atoms; and the other of R$_2$ or R$_3$ is hydrogen; alkyl of from one to six carbon atoms; cyclopropyl; cyclobutyl; cyclopentyl; cyclohexyl; phenyl; or phenyl substituted with fluorine, chlorine, bromine, hydroxyl; trifluoromethyl; alkyl of from one to four carbon atoms, alkoxy of from one to four carbon atoms, or alkanoyloxy of from two to eight carbon atoms.

R$_4$ is alkyl of from one to six carbon atoms; cyclopropyl; cyclobutyl; cyclopentyl; cyclohexyl; or trifluoromethyl.

Also contemplated as falling within the scope of the present invention are the hydroxy acids, and pharmaceutically acceptable salts thereof, derived from the opening of the lactone ring of the compounds of structural formula I above.

In another aspect of the present invention, there is provided a method of preparing the compounds of structural formula I above which comprises the steps of
(a) first reacting a substituted [(pyrrol-1-yl)alkyl]aldehyde compound of the formula

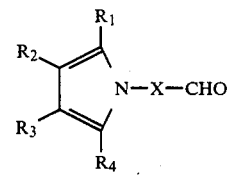

with the dilithio or sodio-lithio salt of methyl acetoacetate to form a compound of the structure

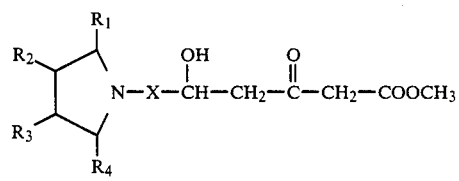

(b) reducing the product of step (a) with a trialkylborane compound such as tributylborane in the presence of sodium borohydride in an inert solvent;

(c) oxidizing the product of step (b) with alkaline aqueous hydrogen peroxide solution to produce a compound of the formula

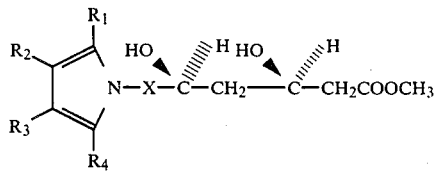

and (d) cyclizing the product step (c) to a lactone of formula I above by heating in an inert solvent such as toluene or, alternatively converting the product of step (c) to a pharmaceutically acceptable salt by conventional methods.

In yet another aspect, the present invention provides pharmaceutical compositions useful as hypolipidemic or hypocholesterolemic agents comprising a hypolipidemic or hypocholesterolemic effective amount of a compound in accordance with this invention as set forth above, in combination with a pharmaceutically acceptable carrier.

In another aspect, the present invention provides a method of inhibiting cholesterol biosynthesis in a patient in need of such treatment by administering an effective amount of a pharmaceutical composition as defined above.

DETAILED DESCRIPTION

The compounds of the present invention comprise a class of trans-6-[2-(3- or 4-carboxamidosubstituted pyrrol-1-yl)alkyl]-4-hydroxypyran-2-ones in which the pyran-2-one moiety is attached, through an alkyl chain, to the substituted pyrrole nucleus at the nitrogen, or 1-position, of the pyrrole. The alkyl group may be methylene, ethylene, propylene, or methylethylene. The preferred alkyl chain linking the substituted pyrrole nucleus and the 4-hydroxypyran-2-one ring is ethylene.

The compounds of structural formula I above possess two asymmetric carbon centers, one at the 4-hydroxy position of the pyran-2-one ring, and the other at the 6-position of the pyran-2-one ring where the alkylpyrrole group is attached. This asymmetry gives rise to four possible isomers, two of which are the R-cis- and S-cis-isomers and the other two of which are the R-trans- and S-trans-isomers. This invention contemplates only the trans- form of the compounds of formula I above.

In the compounds of the present invention, position 2 of the substituted pyrrole nucleus is substituted with 1-naphthyl; 2-naphthyl; cyclohexyl; norbornenyl; 2-, 3-, or 4-pyridinyl; phenyl, phenyl substituted with fluorine, chlorine, bromine, hydroxyl; trifluoromethyl; alkyl of from one to four carbon atoms, alkoxy of from one to four carbon atoms, or alkanoyloxy of from two to eight carbon atoms. Preferred substituent groups at the 2-position of the pyrrole nucleus are phenyl and substituted phenyl.

In the compounds of this invention, position 5 of the pyrrole nucleus is substituted with alkyl of from one to six carbon atoms; cyclopropyl; cyclobutyl; cyclopentyl; cyclohexyl; or trifluoromethyl. Preferred substituents are alkyl or trifluoromethyl with isopropyl being particularly preferred.

The preferred reaction sequence which is used to prepare compounds of the present invention involves the cycloaddition of a disubstituted acetylene, in which one substituent is carboxamido or N-substituted carboxamido, to an appropriately substituted N-acylaminocarboxylic acid to form a substituted pyrrole. This addition may occur in either of two ways, leading to a substituted pyrrole addition product in which the carboxamido substituent resides on either carbon 3 or 4 of the pyrrole nucleus.

Thus, in compounds of the present invention, the substituent at either position 3 or 4 of the pyrrole nucleus is —CONR$_5$R$_6$ where R$_5$ and R$_6$ are independently hydrogen; alkyl of from one to six carbon atoms; 2-, 3-, or 4-pyridinyl; phenyl; phenyl substituted with fluorine, chlorine, bromine, cyano, trifluoromethyl, or carboalkoxy of from three to eight carbon atoms and the other of the two positions is unsubstituted or is substituted with alkyl of from one to six carbon atoms; cyclopropyl; cyclobutyl; cyclopentyl; cyclohexyl; phenyl; or phenyl substituted with fluorine, chlorine, bromine, hydroxyl; trifluoromethyl; alkyl of from one to four carbon atoms, alkoxy of from one to four carbon atoms, or alkanoyloxy of from two to eight carbon atoms.

Preferred groups for R$_5$ and R$_6$ are hydrogen, phenyl, or substituted phenyl. In a particularly preferred group of compounds within the present invention, R$_5$ is hydrogen and R$_6$ is phenyl or substituted phenyl.

The compounds of this invention are prepared by the general reaction scheme outlined in Reaction Sequence 1 which takes advantage of the chemistry of mesionic compounds of the type described originally by R. Huisgen et al., *Ang. Chem. Int. Ed.*, 3: 136 (1964).

The known, or readily prepared, α-haloesters of structural formula II are reacted with the known 2-[1-(2-aminoalkyl)]-1,3-dioxalane, III, in the presence of an acid scavenger such as triethylamine to produce the N-alkyl-α-aminoesters, IV. The aminoesters, IV are

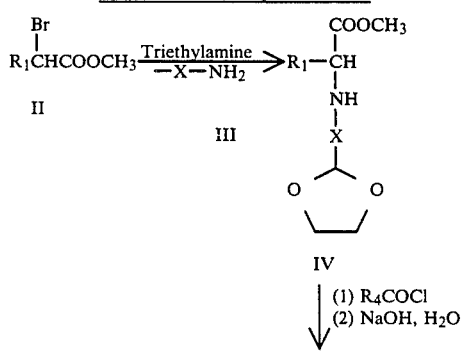

-continued
REACTION SEQUENCE I

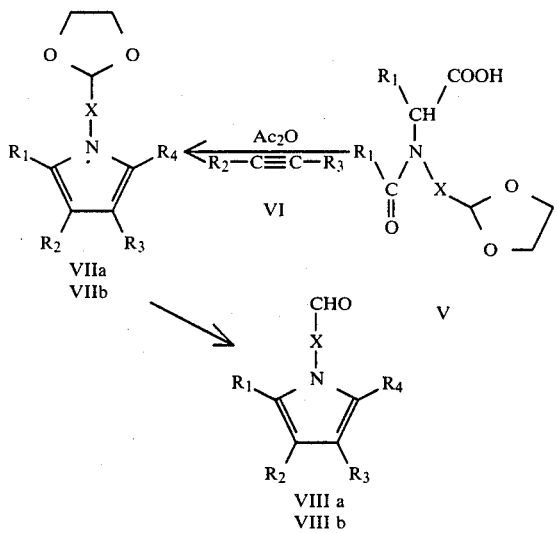

acylated with an acid halide and subsequently hydrolyzed in aqueous base solution to produce the N-acyl-N-alkyl aminoacids, V.

The N-acyl-N-alkyl aminoacids, V, are reacted with the appropriately substituted carboxamido acetylenic compounds, VI, in the presence of an acid anhydride to produce a mixture of the isomeric substituted pyrrole compounds VIIa and VIIb. Depending upon the substituents present, this cyclo-addition reaction affords differing ratios of the two products. For example, in the situation where $R_4$ is trifluoromethyl, the reaction yields roughly equimolar amounts of the two isomeric products. In such situations, the two isomeric products are separated by chromatographic techniques well known in the art, and subsequently further purified, if desired, by recrystallization. On the other hand, in the case where $R_4$ is 1-methylethyl, the cyclo-addition reaction yields predominantly one product which can be purified by recrystallization alone.

Hydrolysis of the acetal function of compounds VIIa and VIIb in aqueous acid solution affords the aldehydes VIIIa and VIIIb. The aldehydes, VIII, are further converted to compounds of the present invention by the processes depicted in Reaction Sequence 2.

The aldehyde compounds, VIII, are reacted with the dilithium or lithio-sodio salt of methyl acetoacetate to produce the corresponding 7-(substituted-pyrrolyl)-5-hydroxy-3-oxoheptanoates, IX. The heptanoates, IX, are dissolved in a polar solvent such as tetrahydrofuran, through which a small amount of air has been bubbled. A slight excess of a trialkylborane, such as tributylborane, is added to the mixture which is then cooled to a temperature of preferably between about 0° C. and −78° C. after which sodium borohydride is added.

The mixture is stirred for about one to two hours and then oxidized by the addition of basic aqueous hydrogen peroxide solution. The reaction produces the 7-(substituted-pyrrolyl)-3,5-dihydroxyheptanoic acids,

REACTION SEQUENCE II

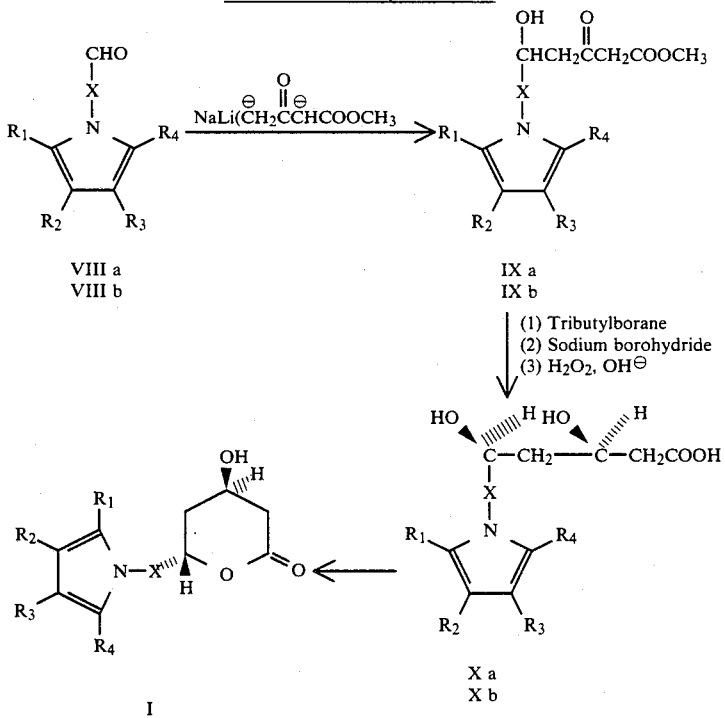

X, in which the product contains a predominance of the desired R*,R* configuration at carbon atoms three and five which bear the hydroxy groups.

The acids may be converted to a corresponding pharmaceutically acceptable salt by conventional means, if desired, or cyclized to the trans-6-[2-(substituted-pyrrol-1-yl)alkyl]pyran-2-ones, I, by dehydration in an inert solvent such as refluxing toluene with azeotropic removal of water. This cyclization step has been found to produce material containing from 85–90% of the desired trans-configuration of the 4-hydroxy group relative to the 6-(substituted-pyrrol-1-yl)alkyl group on the pyran-2-one lactone ring.

The ring-opened hydroxy acids of structural formula II above are intermediates in the synthesis of the lactone compounds of formula I and may be used in their free acid form or in the form of a pharmaceutically acceptable metal or amine salt in the pharmaceutical method of the present invention. These acids react to form pharmaceutically acceptable metal and amine salts. The term "pharmaceutically acceptable metal salt" contemplates salts formed with the sodium, potassium, calcium, magnesium, aluminum, iron, and zinc ions. The term "pharmaceutically acceptable amine salt" contemplates salts with ammonia and organic nitrogenous bases strong enough to form salts with carboxylic acids. Bases useful for the formation of pharmaceutically acceptable nontoxic base addition salts of compounds of the present invention form a class whose limits are readily understood by those skilled in the art.

The free acid form of compounds of the present invention may be regenerated from the salt form, if desired, by contacting the salt with a dilute aqueous solution of an acid such as hydrochloric acid.

The base addition salts may differ from the free acid forms of the compounds of this invention in such physical characteristics as solubility and melting point, but are otherwise considered equivalent to the free acid form for the purposes of this invention.

The compounds of the present invention may exist in solvated or unsolvated form. In general, the solvated forms with pharmaceutically acceptable solvents such as water, ethanol and the like, are equivalent to the unsolvated forms for the purposes of this invention.

The compounds of this invention are useful as hypocholesterolemic or hypolipidemic agents by virtue of their ability to inhibit the biosynthesis of cholesterol through inhibition of the enzyme 3-hydroxy-3-methylglutaryl-coenzyme A reductase (HMG-CoA reductase).

The ability of compounds of the present invention to inhibit the biosynthesis of cholesterol was measured by two methods. A first method (designated CSI screen) utilized the procedure described by R. E. Dugan et al., *Archiv. Biochem. Biophys.*, (1972), 152, 21–27. In this method, the level of HMG-CoA enzyme activity in standard laboratory rats is increased by feeding the rats a chow diet containing 5% cholestyramine for four days, after which the rats are sacrificed.

The rat livers are homogenized, and the incorporation of cholesterol-$^{14}$C-acetate into nonsaponifiable lipid by the rat liver homogenate is measured. The micromolar concentration of compound required for 50% inhibition of sterol synthesis over a one-hour period is measured, and expressed as an $IC_{50}$ value.

A second method (designated COR screen) employed the procedure detailed by T. Kita, et al., *J. Clin. Invest.*, (1980), 66: 1094–1100. In this method, the amount of $^{14}$C-HMG-CoA converted to $^{14}$C-mevalonate in the presence of a purified enzyme preparation of HMG-CoA reductase was measured. The micromolar concentration of compound required for 50% inhibition of cholesterol synthesis was measured and recorded as an $IC_{50}$ value.

The activity of several representative examples of compounds in accordance with the present invention appears in Table 1, and is compared with that of the prior art compound, compactin.

For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is

TABLE 1

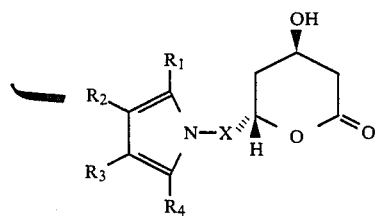

| | | | | | | $IC_{50}$ (Micromoles/liter) | |
|---|---|---|---|---|---|---|---|
| Compound | X | $R_1$ | $R_2$ | $R_3$ | $R_4$ | CSI | COR |
| 1 | —$CH_2CH_2$— | (4-F-phenyl) | (phenyl) | —CONH(phenyl) | —$CH(CH_3)_2$ | 0.035 | 0.050 |

TABLE 1-continued

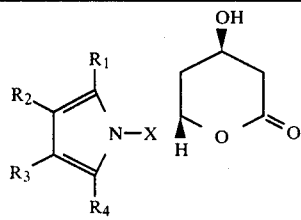

| Compound | X | R₁ | R₂ | R₃ | R₄ | IC₅₀ (Micromoles/liter) CSI | COR |
|---|---|---|---|---|---|---|---|
| 2 | —CH₂CH₂— | 4-F-phenyl | —CONH-phenyl | phenyl | —CF₃ | 0.40 | 0.40 |
| 3 | —CH₂CH₂— | 4-F-phenyl | phenyl | —CONH-phenyl | —CF₃ | 0.018 | 0.020 |
| Compactin (Prior art) | | | | | | 0.026 | 0.028 | surrounded by a carrier, which is thus in association with it. In a similar manner, cachets are also included. Tablets, powders, cachets, and capsules can be used as solid dosage forms suitable for oral administration.

Liquid form preparations include solutions suitable for oral or parenteral administration, or suspensions and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as hypolipidemic or hypocholesterolemic agents, the compounds utilized in the pharmaceutical method of this invention are administered to the patient at dosage levels of from 40 mg to 600 mg per day. For a normal human adult of approximately 70 kg or body weight, this translates to a dosage of from about 0.5 mg/kg to about 8.0 mg/kg of body weight per day.

The dosages, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLE 1

Preparation of trans-5-(4-fluorophenyl)-2-(1-methylethyl)-N,4-diphenyl-1-[2-(tetrahydro-4-hydroxy-6-oxo2H-pyran-2-yl)ethyl]-pyrrole-3-carboxamide Step A: Preparation of α-[[2-(1,3-dioxalan-2-yl)ethyl]amino]-4-fluorobenzeneacetic acid, ethyl ester A solution of 26 g (220 mmol) of 2-[1-(2-aminoethyl)]-1,3-dioxalane in 50 ml of acetonitrile was added at room temperature with stirring to a solution of 200 mmol of α-bromo-4-fluorobenzeneacetic acid, ethyl ester (J. W. Epstein et al., *J. Med. Chem.*, 24: 481–490 (1981)) and 42 ml (300 mmol) of triethylamine in 350 ml of acetonitrile. The resulting mixture was stirred at room temperature overnight and then poured into 500 ml of diethyl ether. The resulting suspension was extracted with 300 ml of water and then twice with 300-ml portions of 2M hydrochloric acid. The combined extracts were made basic with 25% aqueous sodium hydroxide solution and extracted twice with 500-ml portions of ethyl acetate. The ethyl acetate extracts were combined, washed successively with water and brine, and then dried over anhydrous magnesium sulfate. The drying agent was removed by filtration, and the residue concentrated to yield 49.5 g of α-[[2-(1,3-dioxalan-2-yl)ethyl]amino]-4-fluorobenzeneacetic acid, ethyl ester.

The 90 MHz proton magnetic resonance spectrum of the product in deuterochloroform exhibited signals at 1.18 (triplet, 3H, J=7 Hz); 1.85 (multiplet, 2H); 2.20

(broad singlet, 1H); 2.6 (multiplet, 2H); 3.85 (multiplet, 4H); 4.1 (quartet, 2H, J=7 Hz); 4.22 (singlet, 1H); 4.83 (triplet, 1H, J=4.5 Hz); and 6.8-7.3 (multiplet, 4H) parts per million downfield from tetramethylsilane.

Step B. Preparation of α-[[2-(1,3-dioxolan-2-yl)ethyl]-(2-methyl-1-oxopropyl)amino]-4-fluorobenzeneacetic acid, ethyl ester.

Thirty grams (100 mmol) of α-[[2-(1,3-dioxalan-2-yl)ethyl]amino]-4-fluorobenzeneacetic acid, ethyl ester from Step A were dissolved in 200 ml of dichloromethane together with 28.6 ml (205 mmol) of triethylamine and the resulting mixture was cooled to 0° C. under dry nitrogen. A solution of 11 ml (105 mmol) of isobutyryl chloride in 50 ml of dichloromethane was slowly added with stirring. After addition was complete, the mixture was stirred for an additional 60 minutes and then poured into 100 ml of diethyl ether. The ether solution was washed successively with portions of water, 2M hydrochloric acid, sodium bicarbonate solution, and brine, and then dried over anhydrous magnesium sulfate. Evaporation of the solvents yielded 35 g of α-[[2-(1,3-dioxolan-2-yl)-ethyl]-(2-methyl-1-oxopropyl)amino]-4-fluorobenzene-acetic acid, ethyl ester.

The 90 MHz proton magnetic resonance spectrum of a deuterochloroform solution of the product exhibited signals at 1.2 (multiplet, 9H); 1.7 (multiplet, 2H); 2.85 (multiplet, 1H); 3.35 (multiplet, 2H); 3.80 (multiplet, 4H); 4.20 (quartet, 2H, J=7 Hz); 4.60 (triplet, 1H, J=4.5 Hz); 5.81 (singlet, 1H); and 6.8-7.3 (multiplet, 4H) parts per million downfield from tetramethylsilane.

Step C. Preparation of α-[[2-(1,3-dioxolan-2-yl)ethyl]-(2-methyl-1-oxopropyl)amino]-4-fluorobenzeneacetic acid A solution of 35 g (95.3 mmol) of the ester from Step B and 12 g (300 mmol) of sodium hydroxide in 480 ml of 5:1 methanol water was heated under reflux and stirred for two hours. The solution was cooled to room temperature, concentrated, and diluted by the addition of 500 ml of water. The resulting solution was extracted with ether and the aqueous layer was acidified with ice-cold 6M hydrochloric acid and then extracted twice with 300-ml portions of ethyl acetate.

The combined extracts were washed with brine, dried over anhydrous magnesium sulfate, and evaporated to yield 30 g of crude α-[[2-(1,3-dioxolan-2-yl)ethyl]-(2-methyl-1-oxopropyl)amino]-4-fluorobenzeneacetic acid which was used without further purification.

The 90 MHz proton magnetic resonance spectrum of a deuterochloroform solution of the product exhibited signals at 1.11 (doublet, 6H, J=7 Hz); 1.4-1.9 (multiplet, 2H); 2.85 (multiplet, 1H); 3.32 (multiplet, 2H); 3.75 (multiplet, 4H); 4.52 (triplet, 1H, J=4.5 Hz); 5.73 (singlet, 1H); and 6.8-7.3 (multiplet, 4H) parts per million downfield from tetramethylsilane.

Step D. Preparation of N,3-diphenylpropynamide

A solution of 171 mmol of dicyclohexylcarbodiimide in 250 ml of dichloromethane was added dropwise over a two hour period at 0° C. to a suspension of 171 mmol of propiolic acid, 179.6 mmol of aniline, and 5 mmol of 4-dimethylaminopyridine in 400 ml of dichloromethane. After addition was complete, the mixture was stirred for an additional 30 minutes and then diluted with diethyl ether. The resulting mixture was filtered through silica gel, concentrated, and the residue recrystallized to provide 30.5 g of N,3-diphenyl-2-propynamide, mp 122°-123° C.

Analyzed for $C_{15}H_{13}NO$: Calc.: C, 80.69%; H, 5.87%; N, 6.27%; Found: C, 80.54%; H, 5.58%; N, 6.52%.

The infrared spectrum of a KBr pellet of the compound showed principal peaks at 2215, 1630, 1595, 1549, 1490, 1445, 1330, 756, and 691 reciprocal centimeters.

Step E. Preparation of 1-[2-(1,3-dioxalan-2-yl)ethyl]-5-(4-fluorophenyl)-2-(1-methylethyl)-N,4-diphenyl-1H-pyrrole-3-carboxamide A solution of 95 g (280 mmol) of α-[[2-(1,3-dioxolan-2-yl)ethyl]-(2-methyl-1-oxopropyl)amino]-4-fluorobenzeneacetic acid, prepared as described in Step C above, and 98 g (439 mmol) of N,2-diphenylpropenoic carboxamide, prepared as described in Step D above, was heated at 90° C. with stirring for four hours, (Vigorous gas evolution occurred for two hours.) After this time, the mixture was cooled to room temperature and chromatographed twice on silica gel, eluting with 4:1 hexane:ethyl acetate to separate the product ($R_f$=0.35) from the starting material ($R_f$=0.5).

Recrystallization of the product from isopropyl ether provided 59.5 g (119.3 mmol) of 1-[2-(1,3-dioxalan-2-yl)ethyl]-5-(4-fluorophenyl)-2-(1-methylethyl)-N,4-diphenyl-1H-pyrrole-3-carboxamide, mp 159°-162° C.

Analyzed for $C_{31}H_{31}FN_2O_3$: Calc.: C, 74.68%; H, 6.27%; N, 5.62%; Found: C, 75.04%; H, 6.12%; N, 5.89%.

Step F. Preparation of 5-(4-fluorophenyl)-2-(1-methylethyl)-1-(3-oxopropyl)-N,4-diphenyl-1H-pyrrole-3-carboxamide A solution of 59 g (118.3 mmol) of 1-[2-(1,3-dioxalan-2-yl)ethyl]-5-(4-fluorophenyl)-2-(1-methylethyl)-N,4-diphenyl-1H-pyrrole-3-carboxamide, from Step E above, and 0.4 ml of concentrated hydrochloric acid in 1200 ml of anhydrous ethanol was heated under reflux with stirring for 24 hours. After this time the mixture was cooled to room temperature, concentrated, and the residue taken up in 1200 ml of 3:1 acetone:water and 5 g of p-toluenesulfonic acid was added. This mixture was heated under reflux with stirring for two days after which time the solution was cooled to room temperature and partitioned between 1 liter of diethyl ether and 200 ml of brine solution.

The organic phase was separated, washed successively with sodium bicarbonate solution and brine, dried over anhydrous magnesium sulfate and concentrated. The oil which resulted was dissolved in the minimum amount required of hot isopropyl ether. The crystals which formed upon cooling were collected by filtration to yield 36.8 g of 5-(4-fluorophenyl)-2-(1-methylethyl)-1-(3-oxopropyl)-N,4-diphenyl-1H-pyrrole-3-carboxamide. A further crop of 9.8 g of crystals were obtained from the mother liquor.

Analyzed for $C_{29}H_{27}FN_2O_3$: Calc.: C, 76.63%; H, 5.99%; N, 6.16%; Found: C, 76.48%; H, 6.20%; N, 6.14%.

Step G. Preparation of 2-(4-fluorophenyl)-δ-hydroxy-5-(1-methylethyl)-β-oxo-3-phenyl-4-[(phenylamino)carbonyl]-1H-pyrrole-1-heptanoic acid, methyl ester A solution of methyl acetoacetate (26.4 ml, 243 mmol) in 250 ml of anhydrous tetrahydrofuran was added dropwise to a stirred suspension of hexane-washed sodium hydride (6.4 g, 267 mmol) in 200 ml of tetrahydrofuran at 0° C. When gas evolution was complete, 97.2 ml of 2.5M n-butyl lithium was added dropwise over a period of 60 minutes.

The resulting solution was stirred for 30 minutes at 0° C. and then cooled to −78° C. after which a solution of 36.8 g (80.9 mmol) of 5-(4-fluorophenyl)-2-(1-methylethyl)-1-(3-oxopropyl)-N,4-diphenyl-1H-pyrrole-3-carboxamide, from Step F above, in 100 ml of tetrahydrofuran was added over a period of thirty minutes. The resulting solution was stirred for 30 minutes at −78° C. and then warmed to 0° C. where it was held for an additional 60 minutes.

The mixture was then acidified by the dropwise addition of 300 ml of ice-cold 3M hydrochloric acid, diluted with ether, washed successively with water and brine, dried over anhydrous magnesium sulfate, and concentrated. Flash chromatography of the residue yielded 37.9 g of 2-(4-fluorophenyl)-δ-hydroxy-5-(1-methylethyl)-β-oxo-3-phenyl-4-[(phenylamino)carbonyl]-1H-pyrrole-1-heptanoic acid, methyl ester.

The 90 MHz proton magnetic resonance spectrum of the product exhibited signals at 1.50 (doublet, 6H, J=7 Hz); 1.8 (multiplet, 2H); 2.45 (doublet, 2H, J=7 Hz); 2.8 (broad, 1H); 3.33 (singlet, 2H); 3.5 (multiplet, 1H); 3.67 (singlet, 3H); 3.8–4.0 (multiplet, 2H); and 6.8–7.3 (multiplet, 14H) parts per million downfield from tetramethylsilane.

Step H. Preparation of R*,R*-2-(4-fluorophenyl-β,δ-dihydroxy-5-(1-methylethyl)-3-phenyl-4-[(phenylamino)carbonyl]-1H-pyrrole-1-heptanoic acid and trans-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide Air (60 ml) was bubbled via a syringe through a solution of 2-(4-fluorophenyl)-δ-hydroxy-5-(1-methylethyl)-β-oxo-3-phenyl-4-[(phenylamino)carbonyl]-1H-pyrrole-1-heptanoic acid, methyl ester (48 g, 84.1 mmol) and 92.5 ml of 1M tributylborane in 100 ml of anhydrous tetrahydrofuran. The mixture was stirred overnight at room temperature and then cooled to −78° C. Sodium borohydride (3.85 g, 101.8 mmol) was added to the cooled mixture in one portion. The mixture was allowed to warm slowly to 0° C. over a period of three hours, during which there was vigorous gas evolution.

The dry ice-acetone bath applied to the reaction vessel was replaced by an ice bath and 18.3 ml of glacial acetic acid were added dropwise, followed by 204 ml of 3M aqueous sodium hydroxide solution and 30.5 ml of 30% aqueous hydrogen peroxide solution.

The mixture was vigorously stirred while being allowed to warm to room temperature overnight. The mixture was then partitioned between diethyl ether and water and the aqueous layer was separated, acidified, and extracted with ethyl acetate.

The ethyl acetate extract was washed with brine, dried, and evaporated to yield crude R*,R*-2-(4-fluorophenyl-β,δ-dihydroxy-5-(1-methylethyl)-3-phenyl-4-[(phenylamino)carbonyl]-1H-pyrrole-1-heptanoic acid which was used without further purification.

The crude acid was taken up in toluene and lactonized by heating under reflux for six hours. This mixture was chromatographed to provide 30 g of trans-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide as a foamy solid, mp 90°–97° C.

Analyzed for $C_{33}H_{33}FN_2O_4$: Calc.: C, 73.31%; H, 6.15%; N, 5.18%; Found: C, 73.46%; H, 6.31%; N, 5.28%.

This material was found by HPLC analysis to comprise a 9:1 molar ratio of the cis- and trans-isomeric forms of the product. Recrystallization from toluene-ethyl acetate yield the essentially pure trans-form, mp 148°–149° C.

EXAMPLE 2

Preparation of R*,R*-2-(4-fluoro-phenyl-β,δ-dihydroxy-5-(1-methylethyl)-3-phenyl-4-[(phenylamino)carbonyl]-1H-pyrrole-1-heptanoic acid, sodium salt A mixture of trans-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide (10 g, 18.5 mmol) and 0.74 g (18.5 mmol) of sodium hydroxide in 90 ml of a 1:2 mixture of tetrahydrofuran-water was cooled to 0° C. This mixture was allowed to warm slowly to 25° C., after which time it was concentrated and the residual solid dried under vacuum.

The infrared spectrum of the product exhibited principal absorption peaks at 3400, 1651, 1598, 1565, 1511, 1438, 1412, 1316, 1224, 1159, 844, 754, and 702 reciprocal centimeters.

The 90 MHz proton magnetic resonance spectrum of a hexadeutero dimethylsulfoxide solution of the product exhibited signals at 1.34 (doublet, J=7 Hz, 6H); 1.5 (multiplet, 4H); 1.80 (doublet of doublets, J=15, 8 Hz, 1H); 1.99 (doublet of doublets, J=15, 4 Hz, 1H); 3–4 (multiplet, 8H); 6.9–7.3 (multiplet, 12H); 7.50 (doublet, J=8 Hz, 2H); and 9.85 (singlet, 1H) parts per million downfield from tetramethylsilane.

EXAMPLES 3 AND 4

Preparation of trans-2-(4-fluorophenyl)-N,4-diphenyl-1-[2-(tetrahydro-4-hydroxy-6-oxo-2H-pyran-2-yl)ethyl]-5-(trifluoromethyl)-pyrrole-3-carboxamide and trans-5-(4-fluorophenyl)-N,4-diphenyl-1-[2-(tetrahydro-4-hydroxy-6-oxo-2H-pyran-2-yl)ethyl]-2-(trifluoromethyl)pyrrole-3-carboxamide Step A. Preparation of α-[[2-(1,3-dioxalan-2-yl)ethyl]amino]-4-fluorobenzeneacetic acid.

α-[[2-(1,3-Dioxolan-2-yl)ethyl]amino]-4-fluorobenzeneacetic acid, ethyl ester (36.5 g, 122.8 mmol, prepared as described above in Example 1, Step A) was dissolved in 1500 ml of a 5:1 mixture of methanol-water together with 7.6 g of sodium hydroxide. This mixture was heated under reflux for a period of two and one-half hours after which time the solvents were removed under vacuum.

The solid residue was taken up in 325 ml of water and a mixture of 14 ml of glacial acetic in 28 ml of water was added with stirring. After stirring for a time, an additional 3 ml of glacial acetic acid were added and the mixture was chilled for 75 minutes. The solids were collected by filtration, washed with water and then ethyl acetate and dried to yield α-[[2-(1,3-dioxalan-2-yl)ethyl]amino]-4-fluorobenzeneacetic acid, mp 218°–220° C.

Step B. Preparation of a mixture of 5-(4-fluorophenyl)-1-(3-oxopropyl)-N,4-diphenyl-2-(trifluoromethyl)-1H-pyrrole-3-carboxamide and 2-(4-fluorophenyl)-1-(3-oxopropyl)-N,4-diphenyl-5-(trifluoromethyl)-1H-pyrrole-3-carboxamide α-[[2-(1,3-Dioxalan-2-yl)ethyl]amino]-4-fluorobenzeneacetic acid (6.06 g, 22.5 mmol) was dissolved in 45 ml of trifluoroacetic anhydride and 7.47 g (33.8 mmol) of N,3-diphenyl-2-propynamide (prepared as described above in Example 1, Step D) was added. The resulting mixture was heated under reflux for a period of five and one-half hours. The mixture was then cooled, and 1.74 ml of trifluoroacetic acid were added and the mixture was stirred overnight.

The excess trifluoroacetic anhydride was removed under vacuum, and water was added, followed by sufficient acetone to give a homogenous solution. This solution was stirred at room temperature for three hours. The mixture was seeded with N,3-diphenyl-2-propynamide, and a precipitate formed. After three hours, this precipitate was removed by filtration.

The acetone was removed from the filtrate under vacuum and the solid residue was taken up in ether, washed successively with two portions of water, two portions of sodium bicarbonate solution, and two portions of brine and dried over anhydrous magnesium sulfate. The ether was removed under vacuum to yield a crude mixture of the two title compounds.

This mixture was separated by column chromatography on 600 g of silica gel, eluting with a 4:1 mixture of hexane-ethyl acetate.

The first fraction eluted was 5-(4-fluorophenyl)-1-(3-oxopropyl)-N,4-diphenyl-2-(trifluoromethyl)-1H-pyrrole-3-carboxamide.

The 90 MHz proton magnetic resonance spectrum of a deuterochloroform solution of this material exhibited signals at 2.73 (triplet, J=7 Hz, 2H); 4.21 (triplet, J=7 Hz, 2H); 6.7–7.3 (multiplet, 5H); 7.40 (singlet, 5H), and 9.43 (singlet, 1H) parts per million downfield from tetramethylsilane.

The second compound eluted from the column was 2-(4-fluorophenyl)-1-(3-oxopropyl)-N,4-diphenyl-5-(trifluoromethyl)-1H-pyrrole-3-carboxamide.

The 90 MHz proton magnetic resonance spectrum of a deuterochloroform solution of this material exhibited signals at 2.67 (triplet, J=7 Hz, 2H); 4.25 (triplet, J=7 Hz, 2H); 7.0–7.3 (multiplet, 14H); and 9.43 (singlet, 1H) parts per million downfield from tetramethylsilane.

Step C. Preparation of trans-2-(4-fluorophenyl)-N,4-diphenyl-1-[2-(tetrahydro-4-hydroxy-6-oxo-2H-pyran-2-yl)ethyl]-5-(trifluoromethyl)-pyrrole-3-carboxamide and trans-5-(4-fluorophenyl)-N,4-diphenyl-1-[2-(tetrahydro-4-hydroxy-6-oxo-2H-pyran-2-yl)ethyl]-2-(trifluoromethyl)-pyrrole-3-carboxamide Employing the general methods detailed in Example 1, Steps G and H, the title compounds were prepared from the aldehyde compounds of this example, Step B.

The elemental analyses of the two title compounds were:

For trans-5-(4-fluorophenyl)-N,4-diphenyl-1-[2-(tetrahydro-4-hydroxy-6-oxo-2H-pyran-2-yl)ethyl]-2-(trifluoromethyl)-pyrrole-3-carboxamide:

Analyzed for $C_{31}H_{26}N_2O_4$: Calc.: C, 65.72%; H, 4.63%; N, 4.94%; Found: C, 65.82%; H, 4.91%; N, 4.69%.

The trans-2-(4-fluorophenyl)-N,4-diphenyl-1-[2-(tetrahydro-4-hydroxy-6-oxo-2H-pyran-2-yl)ethyl]-5-(trifluoromethyl)-pyrrole-3-carboxamide was found, upon recrystallization from toluene to contain 0.25 mols of toluene as solvent of crystallization, mp 106°–111° C.

Analyzed for $C_{31}H_{26}N_2O_4 \cdot 0.25 C_7H_8$: Calc.: C, 66.72%; H, 4.79%; N, 4.72%; Found: C, 66.81%; H, 4.86%; N, 4.60%.

I claim:
1. A compound of structural formula I

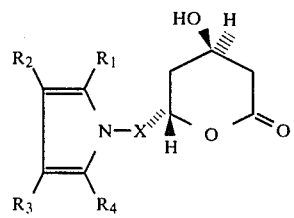

wherein
X is —CH$_2$—, —CH$_2$CH$_2$—, —CH$_2$CH$_2$CH$_2$—, or —CH$_2$CH(CH$_3$)—;
R$_1$ is
1-naphthyl;
2-naphthyl;
cyclohexyl;
norbornenyl;
phenyl;
phenyl substituted with
fluorine,
chlorine,
bromine,
hydroxyl,
trifluoromethyl,
alkyl of from one to four carbon atoms,
alkoxy of from one to four carbon atoms, or
alkanoyloxy of from two to eight carbon atoms;
either of R$_2$ or R$_3$ is —CONR$_5$R$_6$ where R$_5$ and R$_6$ are
independently
hydrogen;
alkyl of from one to six carbon atoms;
phenyl;
phenyl substituted with
fluorine,
chlorine,
bromine,
cyano,
trifluoromethyl, or
carboalkoxy of from three to eight carbon atoms;
and the other of R$_2$ or R$_3$ is
hydrogen;
alkyl of from one to six carbon atoms;
cyclopropyl;
cyclobutyl;
cyclopentyl;
cyclohexyl;
phenyl; or
phenyl substituted with
fluorine,
chlorine,
bromine,
hydroxyl,
trifluoromethyl,
alkyl of from one to four carbon atoms,
alkoxy of from one to four carbon atoms, or
alkanoyloxy of from two to eight carbon atoms;
R$_4$ is
alkyl of from one to six carbon atoms;
cyclopropyl;
cyclobutyl;
cyclopentyl;
cyclohexyl; or
trifluoromethyl;
or a hydroxy acid or pharmaceutically acceptable salts thereof, corresponding to the opened lactone ring of the compounds of structural formula I above.

2. A compound as defined by claim 1 wherein X is —CH$_2$CH$_2$—.

3. A compound as defined by claim 2 wherein R$_1$ is phenyl; or phenyl substituted with fluorine, chlorine, bromine, hydroxyl; trifluoromethyl; alkyl of from one to four carbon atoms, alkoxy of from one to four carbon atoms, or alkanoyloxy of from two to eight carbon atoms.

4. A compound as defined by claim 2 wherein R$_4$ is alkyl of from one to six carbon atoms.

5. A compound as defined by claim 1 having the name trans-($\pm$)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

6. A compound as defined by claim 1 having the name trans-2-(4-fluorophenyl)-N,4-diphenyl-1-[2-(tetrahydro-4-hydroxy-6-oxo-2H-pyran-2-yl)ethyl]-5-trifluoromethyl-1H-pyrrole-3-carboxamide.

7. A compound as defined by claim 1 having the name trans-5-(4-fluorophenyl)-N,4-diphenyl-1-[2-(tetrahydro-4-hydroxy-6-oxo-2H-pyran-2-yl)ethyl]-2-trifluoromethyl-1H-pyrrole-3-carboxamide.

8. A pharmaceutical composition, useful as a hypocholesterolemic agent, comprising a hypocholesterolemic effective amount of a compound in accordance with claim 1 in combination with a pharmaceutically acceptable carrier.

9. A method of inhibiting cholesterol biosynthesis in a patient in need of such treatment by administering a pharmaceutical composition as defined by claim 8.

* * * * *

UNITED STATES PATENT AND TRADEMARK OFFICE

CERTIFICATE EXTENDING PATENT TERM
UNDER 35 U.S.C. § 156

PATENT NO.      :   4,681,893

ISSUED          :   July 21, 1987

INVENTOR(S)     :   Bruce D. Roth

PATENT OWNER    :   Warner-Lambert Company

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

1,213 days from May 30, 2006, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 15th day of July 1998.

Bruce A. Lehman
Assistant Secretary of Commerce and
    Commissioner of Patents and Trademarks

(12) EX PARTE REEXAMINATION CERTIFICATE (6392nd)
United States Patent
Roth

(10) Number: US 4,681,893 C1
(45) Certificate Issued: Aug. 26, 2008

(54) TRANS-6-[2-(3- OR 4-CARBOXAMIDO-SUBSTITUTED PYRROL-1-YL)ALKYL]-4-HYDROXYPYRAN-2-ONE INHIBITORS OF CHOLESTEROL SYNTHESIS

(75) Inventor: Bruce D. Roth, Ann Arbor, MI (US)

(73) Assignee: Warner-Lambert Company, Ann Arbor, MI (US)

Reexamination Request:
No. 90/008,727, Jul. 2, 2007

Reexamination Certificate for:
Patent No.: 4,681,893
Issued: Jul. 21, 1987
Appl. No.: 06/868,867
Filed: May 30, 1986

(51) Int. Cl.
*C07D 405/00* (2006.01)
*C07D 405/06* (2006.01)

(52) U.S. Cl. .................. 514/422; 514/423; 546/256; 546/279.1; 548/517; 548/537

(58) Field of Classification Search .................. None
See application file for complete search history.

(56) References Cited

U.S. PATENT DOCUMENTS

| | | | |
|---|---|---|---|
| 3,634,453 A | * | 1/1972 | McManus et al. ........... 548/486 |
| 3,808,254 A | | 4/1974 | Matthews |
| 3,931,173 A | * | 1/1976 | Parker et al. ................ 544/148 |
| 3,965,129 A | | 6/1976 | Perry et al. |
| 3,983,140 A | | 9/1976 | Endo et al. |
| 4,072,698 A | | 2/1978 | Hylton et al. |
| 4,137,322 A | | 1/1979 | Endo et al. |
| 4,139,555 A | | 2/1979 | Zerbes |
| 4,171,359 A | | 10/1979 | Weinstock |
| 4,192,872 A | | 3/1980 | Weinstock |
| 4,231,938 A | | 11/1980 | Monaghan et al. |
| 4,281,132 A | | 7/1981 | Ward |
| 4,282,155 A | | 8/1981 | Smith et al. |
| 4,293,496 A | | 10/1981 | Willard |
| 4,319,039 A | | 3/1982 | Albers-Schonberg |
| 4,342,761 A | | 8/1982 | Ward |
| 4,342,767 A | | 8/1982 | Albers-Schonberg et al. |
| 4,346,227 A | | 8/1982 | Terahara et al. |
| 4,374,829 A | | 2/1983 | Harris et al. |
| 4,374,844 A | | 2/1983 | McCombie |
| 4,375,475 A | | 3/1983 | Willard et al. |
| 4,444,784 A | | 4/1984 | Hoffman et al. |
| 4,474,971 A | | 10/1984 | Wareing |
| 4,495,103 A | | 1/1985 | Terashima et al. |
| 4,555,511 A | | 11/1985 | Schnorrenberg et al. |
| 4,581,453 A | * | 4/1986 | Ippen et al. ................ 544/331 |
| 4,611,067 A | | 9/1986 | Volante et al. |
| 4,613,610 A | | 9/1986 | Wareing |
| 4,647,576 A | * | 3/1987 | Hoefle et al. ................ 514/422 |
| 4,681,893 A | | 7/1987 | Roth |
| 4,697,036 A | | 9/1987 | Giordano et al. |
| 4,739,073 A | | 4/1988 | Kathawala |
| 4,743,450 A | | 5/1988 | Harris et al. |
| 4,775,681 A | | 10/1988 | Heifetz |
| 4,786,505 A | | 11/1988 | Lovgren et al. |
| 4,853,230 A | | 8/1989 | Lovgren et al. |
| 4,898,868 A | | 2/1990 | Bergmann et al. |
| 4,950,775 A | | 8/1990 | Heathcock et al. |
| 4,962,115 A | | 10/1990 | Van Daele |
| 4,976,949 A | | 12/1990 | Meyer et al. |
| 4,978,791 A | | 12/1990 | Völker et al. |
| 4,992,462 A | | 2/1991 | Hubsch et al. |
| 5,003,080 A | | 3/1991 | Butler et al. |
| 5,004,651 A | | 4/1991 | Becker |
| 5,006,530 A | | 4/1991 | Angerbauer et al. |
| 5,030,447 A | | 7/1991 | Joshi et al. |
| 5,045,321 A | | 9/1991 | Makino et al. |
| 5,055,484 A | | 10/1991 | Jendralla et al. |
| 5,061,722 A | | 10/1991 | Teetz et al. |
| 5,093,132 A | | 3/1992 | Makino et al. |
| 5,097,045 A | | 3/1992 | Butler et al. |
| 5,124,482 A | | 6/1992 | Butler et al. |
| 5,149,837 A | | 9/1992 | Butler et al. |
| 5,151,433 A | | 9/1992 | Fulbreth et al. |
| 5,208,258 A | | 5/1993 | Heathcock et al. |
| 5,216,174 A | | 6/1993 | Butler et al. |
| 5,245,047 A | | 9/1993 | Butler et al. |
| 5,273,995 A | | 12/1993 | Roth |
| 5,280,126 A | | 1/1994 | Butler et al. |
| 5,354,772 A | | 10/1994 | Kathawala |
| 5,378,729 A | | 1/1995 | Kohn et al. |
| 5,395,847 A | | 3/1995 | Weinstock et al. |
| 5,969,156 A | | 10/1999 | Briggs |
| 6,087,511 A | | 7/2000 | Lin et al. |
| 6,121,461 A | | 9/2000 | McKenzie et al. |
| 6,274,740 B1 | | 8/2001 | Lin et al. |
| 6,605,729 B1 | | 8/2003 | Byrn et al. |
| 5,969,156 C1 | | 9/2006 | Briggs et al. |
| 7,144,915 B2 | | 12/2006 | Byrn et al. |

FOREIGN PATENT DOCUMENTS

| | | |
|---|---|---|
| AU | 601981 | 9/1990 |
| AU | 621874 | 3/1992 |
| CA | 1161380 | 1/1984 |
| CA | 1268768 | 5/1990 |
| CA | 1304080 | 6/1992 |
| CA | 1330441 | 6/1994 |
| CA | 2021546 | 4/1997 |
| CA | 2465565 | 12/2004 |
| DK | 0 171 588 | 12/1987 |
| DK | 171588 B1 | 2/1997 |
| EP | 0 024 348 | 3/1981 |

(Continued)

OTHER PUBLICATIONS

Reissue application and related papers, U.S. Appl. No. 11/653,830, filed Jan. 16, 2007 (Reissue of U.S. Patent 5,273,995).

(Continued)

*Primary Examiner*—Evelyn Huang

(57) ABSTRACT

Certain trans-6-[2-(3- or 4-carboxamido-substituted pyrrol-1-yl)alkyl]-4-hydroxypyran-2-ones and the corresponding ring-opened acids derived therefrom which are potent inhibitors of the enzyme 3-hydroxy-3-methylglutaryl-coenzyme A reductase HMG CoA reductase and are thus useful hypolipidemic or hypocholesterolemic agents. Pharmaceutical compositions containing such compounds, and a method of inhibiting the biosynthesis of cholesterol employing such pharmaceutical compositions are also disclosed.

FOREIGN PATENT DOCUMENTS

| | | |
|---|---|---|
| EP | 0 114 027 A1 | 7/1984 |
| EP | 0 171 588 A1 | 2/1986 |
| EP | 0179 559 A2 * | 4/1986 |
| EP | 0 211 416 | 2/1987 |
| EP | 0 221 025 A1 | 5/1987 |
| EP | 0 232 997 | 8/1987 |
| EP | 0 247 633 | 12/1987 |
| EP | 0 251 625 | 1/1988 |
| EP | 0 259 086 | 3/1988 |
| EP | 0 319 856 A2 | 6/1989 |
| EP | 0 330 172 | 8/1989 |
| EP | 89103078.5 | 8/1989 |
| EP | 0 409 281 | 1/1991 |
| IE | 1197/87 L | 11/1987 |
| IE | 890391 | 8/1989 |
| JP | 2240/1982 | 1/1982 |
| JP | 10572/1983 | 5/1983 |
| JP | 62-289577 | 12/1987 |
| JP | 72652/1988 | 4/1988 |
| KR | 1987-5372 | 2/1994 |
| PT | 84975 | 6/1987 |
| PT | 89774 | 10/1989 |
| WO | WO 84/02131 | 6/1984 |
| WO | WO 88/07582 | 10/1988 |
| WO | WO 89/07598 | 8/1989 |
| WO | WO 90/00553 | 1/1990 |
| WO | WO 97/03959 | 2/1997 |
| WO | WO 99/47138 | 9/1999 |

OTHER PUBLICATIONS

"Stipulated Amended Order of Final Judgement" dated Dec. 13, 2007 in Civil Action No. 07–138 (JJF), United States District Court for the District of Delaware.
Alberts Am.J.Cardiology vol. 62, 10J–15J (1988).
Alberts Proc Natl Acad Sci USA Jul. 1980;77(7):3957–61.
Ariëns et al. Cholinergic and Anticholinergic Drugs: Do they act on common receptors?, Ann NY Acad Sci, vol. 144, pp. 842–868 (1967).
Ariëns Stereochemistry and Biological Activity of Drugs, 11–53, 89–102, 161–185 (1983).
Ariëns Stereochemistry, a Basis for Sophisticated Nonsense in Pharmacokinetics and Clinical Pharmacology, Eur. J. Clin. Pharmacol., vol. 26, pp. 663–668 (1984).
Ariëns, E.J., "Implications of the Neglect of Stereochemistry in Pharmacokinetics and Clinical Pharmacology", Drug Intelligence and Clinical Pharmacy, (Oct. 1987), vol. 21, 827–829.
Ariëns, E.J., "Stereochemistry in the Analysis of Drug–Action. Part II.", Medicinal Research Reviews, (1987), vol. 7, No. 3, 367–387.
Ariëns, E.J., "Stereochemistry: A Source of Problems in Medicinal Chemistry", Medicinal Research Reviews, (1986), vol. 6, No. 4, 451–466.
Ariëns, Chirality in bioactive agents and its pitfalls, TIPS, Elsevier Publishers B.V., Amsterdam, p. 200–205 (1986).
Audebert Direct Resolution of Enantiomers in Column Liquid Chromatography, J. Liquid Chromatography, vol. 2, No. 8, 1063–1095 (1979).
Banitt, E.H. et al., "Resolution of Flecainide Acetate, N–(2–Piperidylmethyl)–2,5–bi5(2,2,2–trifluoroethoxy)benzamide Acetate, and Antiarrhythmic Properties of the Enantiomers", J. Med. Chem. (1986),29:299–302.
Berge et al. Pharmaceutical Salts, J. Pharm. Sci., vol. 66(1):1–19 (1977).
Braun, M et al., Tetrahedron Lett., 25, 5031–5034 (1984).
Brown, A.G. et al., "Crystal and Molecular Structure of Compactin, a New Antifungal Metabolite from *Penicillium brevicompactum*", J. Chem. Soc. Perkin I, (1976) 1165–1170.
Burger Medicinal Chemistry, Chapter 7, pp. 81–107 (1970).
Carey et al. "Advanced Organic Chemistry", 2nd Ed., Chapter 2 and p. 75 (1984).
Stinson Chemical and Engineering News, 70, Sep. 28, 46 (1992).
Stinson Chemical and Engineering News, 71, Sep. 27, 38 (1993).
Collet et al. Optical Resolution by Direct Crystallization of Enantiomer Mixtures, Chemical Reviews, vol. 80, No. 3, 215–230 (1980).
Conant et al. The Chemistry of Organic Compounds, A Year's Course in Organic Chemistry, $4^{th}$ ed. Macmillan, New York, 1954, p. 234.
Cook Enantioselective Drug Analysis, Pharmacy International, vol. 6, No. 12, pp. 302–305 (1985).
Decamp Chirality, 1989, 1: 2–6.
Demerson et al. Resolution of Etodolac and Antiinflammatory and Prostaglandin Synthetase inhibiting Properties of the Enantiomers, J. Med. Chem., vol. 26, No. 12, 1778–1780 (1983).
Dotsevi, C. et al., "Chromatographic Optical Resolution through Chiral Complexation of Amino Ester Salts by a Host Covalently Bound to Silica Gel", J. Am. Chem. Soc., (1975), 97:1259–1261.
Dugan, R.E. et al., "Factors Affecting the Diurnal Variation in the Level of β–Hydroxy–β–Methylglutaryl Coenzyme A Reductase and Cholesterol–Synthesizing Activity in Rat Liver", Archiv. Biochem. Biophys., (1972), 152:21–27.
Eliel et al., Stereochemistry of Organic Compounds, Wiley, New York, 1994, pp. 329–331, and remainder of Section 7–3.
Eliel et al., Section 3–1—Compounds with One Asymmetric Carbon Atom, Stereochemistry of Carbon Compounds, McGraw–Hill Book Company, Inc. (1962).
Eliel et al., Section 4–4—Resolution of Racemic Modifications, Stereochemistry of Carbon Compounds, McGraw–Hill Book Company, Inc. pp. 47–74 (1962).
Endo, J Med Chem., 28: 401–405 (1985).
Endo, A. et al., "Biochemical Aspect of HMG CoA Reductase Inhibitors", Adv. in Enzyme Regulation, Proceedings of the 28 Symposium on Regulation of Enzyme Activity and Synthesis in Normal and Neoplastic Tissues held at Indiana University School of Medicine, Indianapolis, Indiana, (Oct. 2 and 3, 1988), vol. 28, p. 53–64.
Endo, A. et al., "Inhibition of Cholesterol Synthesis in vitro and in vivo by ML–236A and ML–236B, Competitive Inhibitors of 3–Hydroxy–3–methylglutaryl– Coenzyme A Reductase", Eur. J. Biochem., (1977), 77:31–36.
Endo, A., "Chemistry, Biochemistry, and Pharmacology of HMG–CoA Reductase Inhibitors", Klin. Wochenschr, (1988) 66:421–427.
Falck, J.R. et al., "Total Synthesis of (+)–Dihydromevinolin", Tetrahedron Letters, (1984), vol. 25, No. 33, pp. 3563–3566.
Fessenden et al. Section 4.10—Resolution of a Racemic Mixture, Organic Chemistry, $2^{nd}$ Ed., Willard Grant Press, Boston (1982).
Fieser et al. Organic Chemistry, D. C. Heath, Boston, 2nd ed., 1950, pp. 267–274.

Fogassy, E. et al., "Pseudosymmetry and Chiral Discrimination in Optical Resolution via Diastereoisomeric Salt Formation. The Crystal Structures of (R)– and (S)–N–Methylamphetamine Bitartrates (RMERTA and SMERTA)", J. Chem. Soc. Perkin Trans. II, (1986) 1881–1886.

Gekkan–Yakuji, vol. 29, No. 10, pp. 23–26 (with English translation).

Goldman, M. et al., "Resolution of Chiral Olefinic Hydrocarbons and Sulfoxides by High–Performance Liquid Chromatography via Diastereomeric Platinum Complexes", J. Am. Chem. Soc., (1982) 104:1093–1095.

Gould, P.L., "Salt Selection for Basic Drugs", Int. J. Pharmaceutics, (1986), 33:201–217.

Greene Chapter 6—Preformulation, in Modern Pharmaceutics, Banker and Rhodes, Marcel Dekker Inc., New York.

Grieco, P.A. et al., "Convergent, Enantiospecific Total Synthesis of the Hypocholesterolemic Agent (+)—Compactin", J. Am. Chem. Soc., (1986) 108:5908–5919.

Grieco, P.A. et al., "Total Synthesis of the Hypocholesterolemic Agent (+)—Compactin", J. Am.Chem. Soc., (1983), 105:1403–1404.

Grundy, S.M., "HMG–CoA Reductase Inhibitors for Treatment of Hypercholesterolemia", N.E. J. Med., (Jul. 7, 1988), vol. 319, No. 1, pp. 24–33.

Guindon, Y. et al., "Preparation of ethyl 5(S),6–epoxy–3(R)–(methyoxmethoxy)hexanoate: A key chiral intermediate for mevinolin and compactin", Tetrahedron Letters, (1985), vol. 26, No. 9, pp. 1185–1188.

Heathcock et al. J. Med. Chem. 1987, 30, 1858–1873.

Heathcock et al. J. Med. Chem. 1989, 32, 197–202.

Helmchen et al, Agnew Chem. Int. Edn. 1979. 18, p. 63–65.

Hirama M. et al., "Chiral Total Synthesis of Compactin", J. Am. Chem. Soc., (1982), 104:4251–4253.

Hirama, M. et al., "Total Synthesis of (+)–Monacolin K (Mevinolin)", Tetrahedron Letters, (1983), vol. 24, No. 17, pp. 1811–1812.

Hoeg, J.M. et al., "3.–Hydroxy–3–Methylglutaryl–Coenzyme A Reductase Inhibitors in the Treatment of Hypercholesterolemia", JAMA, (Dec. 25, 1987), vol. 258, No. 24, p. 3532–3536.

Hoffman et al, J. Med. Chem., 29: 159–169 (Feb. 1986).

Hoffman, W.F. et al., "3–hydroxy–3–methylglutaryl–coenzyme A reductase inhibitors. 4. Side Chain Ester Derivatives of Mevinolin", J. Med. Chem. (1986) 29:849–852.

Hsu, C–T, et al., "Total Synthesis of the Hypocholesterolemic Agent Compactin", J. Am. Chem.Soc., (1983), 105:593–601.

Hubbard et al. Chiral Pharmacology and its Consequences for Therapeutic Monitoring, Clin. Biochem., vol. 19, pp. 107–112 (1986).

Jackson et al. Characterization and Antifertility Activity in Rats of S(+) a–Chlorohydrin Chem.–Biol Interactions, vol. 17, No. 1, 117–120 (1977).

Jacques et al Enantiomers, Racemates, and Resolutions, John Wiley & Sons, Toronto (1981).

Jacques et al. Types of Crystalline Racemates, Enantiomers, Racemates, and Resolutions, c.1, 3–23 (1981).

Jacques et al. Formation and Separation of Diastereomers, Enantiomers, Racemates, and Resolutions, c.5, 251–281 (1981).

Jacques et al Section 5.1.2—Resolution of Bases, Enantiomers, Racemates, and Resolutions, John Wiley & Sons, Toronto (1981).

Jacques et al. Experimental Aspects and Art of Resolutions, Enantiomers, Racemates, and Resolutions, c.7, 378–434 (1981).

Johnson et al. Tetrahedron Letters, vol. 29, No. 31, pp. 3757–3760, 1988.

Kalant et al Chapter 9—Drug Receptors, Principles of Medical Pharmacology, 4th ed., University of Toronto Press, Toronto (1985).

Kalant et al Chapter 10—Specificity of Drug Action, Principles of Medical Pharmacology, 4th ed., University of Toronto Press, Toronto (1985).

Kaneko et al. Eur. J. Biochem., 87:313–321 (1978).

Kathawala, E.G., "Exciting Developments in the Area of HMG–CoA Reductase Inhibitors", Trends in Medicinal Chemistry '88: Proceedings of the Xth International Symposium on Medicinal Chemistry, Budapest, Aug. 15–19, 1988, (disclosed at the conference in Aug. 1988), pp. 709–728 (textbook received at CISTI on Jun. 23, 1989).

Kemp et al. Organic Chemistry, Worth, New York, 1980, pp. 172 and 173.

Kim, Y.H. et al., Chiral Differentiation by the P–(+)–Hexahelicene–7–7'–dicarboxylic Acid Disodium Salt. Resolution of N–2,4–Dinitrophenyl–α–amino–acid Esters by High Performance Liquid Chromatography, J. Chem. Soc., Chem. Commun., (1982), p. 1336–1337.

Krause et al. Atherosclerosis, 117:237 (1995).

Lee, TIPS, 8:442–446 (1987).

Lee, T–J, "An expeditious chiral route to analogs of mevinolin and compactin", Tetrahedron Letters, (1985), vol. 26, No. 41, pp. 4995–4996.

Lee, T–J, et al., "Structural Modification of Mevinolin", J. Org. Chem., (1982), 47:4750–4757.

Lehmann et al. Stereoselectivity and Affinity in Molecular Pharmacology, Jucker, E. (ed), Progress in Drug Research, vol. 20, Birkhauser, Basel Stuttgard, pp. 101–142.

Lehmann Stereoselective Molecular Recognition in Biology. Cuatrecasas, P., Greaves M.F. (eds), Receptors and Recognition, vol. 5, Series A, Chapman and Hall, London, pp. 1–77 (1978).

Lim et al. Enantiomeric resolution of di–threo–methylphenidate, U.S.P. (Ritalin®), by high– performance liquid chromatography, J. Chromatography, vol. 328, 378–386 (1985).

Liu et al. Effect of Enantiomeric Purity on Solubility Determination of Dexclamol Hydrochloride, J. Pharm. Sci., vol. 67, pp. 636–638 (1978).

Lynch et al., Tetrahedron Letters, 28: 1385–1388 (1987).

Majewski et al. Tetrahedron Letters, vol. 25, No. 20 pp. 2101–2104, 1984.

Mantell, G., "Lipid Lowering Drugs in Atherosclerosis—The HMG–CoA Reductase Inhibitors", Clin. and Exper. Hyper.–Theory and Practice, (Jan. 1, 1989), vol. 11, Issue 5–6, 927–941.

March Methods of Resolution, in Advanced Organic Chemistry—Reactions, Mechanisms and Structure, 2nd Ed., McGraw Hill, New York 1977, pp. 108–111.

Martindale, The Extra Pharmacopoeia (ed. Reynolds 28th ed. 1982), p. 44.

McBlain et al. Facile Route to the Resolution of the Enantiomers of 1–Chloro–2–[2,2,2–trichloro–1–(4–chlorophenyl) ethyl]benzene (o,p'–DDT), J. Ag. Food Chem., vol. 25, No. 1, 59–63 (1977).

Meyers, A.I., et al., "Separation of Diastereomers Using a Low Cost Preparative Medium–Pressure Liquid Chromatograph", J. Org. Chem., (1979), vol. 44, No. 13, p. 2247–2249.

Morrison et al Section 7.9—Reactions of chiral molecules with optically active reagents. Resolution, Organic Chemistry, 3rd Ed., Allyn and Bacon, Inc., Boston (1973).

Nakamura et al. Biochemistry, 24:1364–1376 (1985).

Narasaka et al. Tetrahedron, 40, 223–2238 (1984).

Pirkle, W.H. et al., "Broad Spectrum Methods for the Resolution of Optical Isomers. A Discussion of the Reasons Underlying the Chromatographic Separability of Some Diastereomeric Carbamates", J. Org. Chem,(1977), vol. 42, No. 11, p. 1839–1844.

Portoghese Relationships between Stereostructure and Pharmacological Activities, Elliott, H.W., Cutting, W.C., Dreisbach, R.H. (eds), Annual Review of Pharmacology, vol. 10, Annual Reviews Inc., Palo Alto, CA, pp. 51–76 (1970).

Prasad, K. et al., "Asymmetric synthesis of (3R–trans)– and (3S–cis)–hydroxy–5–pentanolides", Tetrahedron Letters, (1984), vol. 25, No. 32, pp. 3391–3394.

Prugh et al., Tetrahedron Letters 23: 281–284 (1982).

Ravin Chapter 75—Preformulation, Remington's Pharmaceutical Sciences, 16th Ed., Philadelphia College of Pharmacy and Science (1980).

Repta et al. Utilization of an Enantiomer as a Solution to a Pharmaceutical Problem: Application to Solubilization of 1,2–Di(4–piperazine–2,6–dione)Propane, J. Pharm. Sci., vol. 65, pp. 238–242.

Robinson Absolute configurations of(–+–)– and (–)–1–amino 3–chloropropan–2–ol hydrochlorides, Chemistry and Industry, No. 15, p. 652 (1976).

Rosen, T. et al., "Tetrahedron Report No. 208—The Synthesis of Mevinic Acids", Tetrahedron, (1986), vol. 42, No. 18, pp. 4909–4951.

Roth et al. Tetrahedron Letters, vol. 29, No. 11, pp. 1255–1258 (1988).

Roth, Progress In Med. Chem., 40, 1–22 (2002).

Saigo, K. et al., "Optical Resolution of 2–Amino–1,2–diphenylethanol by Preferential Crystallization and Its Utilization in Fractional Crystallization and Enantioselective Reduction of Prochiral Ketones", Bull.Chem. Soc. Jpn., (1982) 55:1568–1573.

Schneider, C.S. et al., "Dopamine Autoreceptor Agonists: Resolution and Pharmacological Activity of 2,6–Diaminotetrahydrobenzothiazole and an Aminothiazole Analogue of Apomorphine", J. Med. Chem., (1987), 30:494–498.

Serizawa, N. et al., "Microbial Hydroxylation of ML–236B (Compactin) and Monacolin K (MG–530B)", J. Antibiotics, (May 1983), 36:604–607.

Shaw, CDER FDA Guideline for Submitting Supporting Documentation in Drug Applications for the Manufacture of Drug Substances (1987).

Slater, E.E. et al., "Mechanism of Action and Biological Profile of HMG CoA Reductase Inhibitors, A New Therapeutic Alternative", Drugs, (1988) 36 (Suppl. 3):72–82.

Sletzinger, M. et al., "A Diastereospecific, Non–Racemic Synthesis of a Novel β–Hydroxy–σ–Lactone HMG–CoA Reductase Inhibitor", Tetrahedron Letters, (1985), vol. 26, No. 25, pp. 2951–2954.

Stokker et al., J. Med Chem 28:347–358 (1985).

Stokker et al. J. Med. Chem. 1986, 29, 170–181.

Stokker et al. J. Org. Chem, 1986, 51, 4931–4934.

Stokker, G.E. et al., "3–Hydroxy–3–methylglutaryl– coenzyme A Reductase Inhibitors. 5. 6–(Fluoren–9–yl)– and 6–(fluoren–9–ylidenyl)–3,5–dihydroxyhexanoic acids and their lactone derivatives", J. Med. Chem., (May 1986), 29(5):852–855.

Streitwieser et al., Introduction to Organic Chemistry, Macmillan, New York, 3rd ed. 1985, p. 695.

Streitwieser Jr., A., "Stereoisomerism", Introduction to Organic Chemistry, Macmillan, New York, 3rd ed. 1985 Chapter 7, pp. 113–139.

Takano et al. Synthesis, Jul. 1989, vol. 7, p. 539–541.

The Merck Index, 10th Ed., (1983), entry 5949. N–Methylglucamine, p. 870–871.

The Merck Index, 12th Ed., (1996), entry 897. Atorvastatin, p. 146.

Tobert, J.A., "New developments in lipid–lowering therapy: the role of inhibitors of hydroxymethylglutarylcoenzyme A reductase", Circulation, (1987), 76, No. 3, 534–538.

Viret et al. Simple Optical Resolution of Terleucine, Tetrahedron Letters, vol. 27, No. 48, pp. 5865–5868 (1986).

Vollhardt Section 5–7—Resolution: The Separation of Enantiomers, in Organic Chemistry, W.H. Freeman and Company, New York (1987).

Vriesema, B.K. et al., "Resolution of 2–amino–5–thiomethyl pentanoic acid (homomethionine) with aminopeptidase from *pseudomonas putida* or chiral phosphoric acids.", Tetrahedron Letters, (1986), vol. 26, No. 18, p. 2045–2048.

Walking, D. et al., "Decision Analysis in Drug Product Development", Drug & Cosmetic Industry, (1973) 112(3):39–41.

Weissbuch, I. et al., "Design of Polymeric Inhibitors for the Control of Crystal Polymorphism. Induced Enantiomeric Resolution of Racemic Histidine by Crystallization at 25° C.", J. Am. Chem. Soc., (1987) 109:1869–1871.

Wells Pharmaceutical Preformulation: The Physicochemical Properties of Drug Substances—Chapter 2 (1988).

Whilen Topics in Stereochemistry, 6, 107–176 (1971).

Wilen et al. Tetrahedron, 33, 2725–2736 (1977).

Williams, K.M., "Chirality: Pharmacokinetics and Pharmacodynamics in 3 Dimensions", Clinical and Experimental Pharmacology and Physiology, (Jun. 1989), vol. 16, No. 6, pp. 465–470.

Witiak et al., Pharmaceuticals, Optically Active, Encyclopedia of Chemical Technology, 3ed, vol. 17, 311–345 (1982).

Wong, C–H. et al., "Mutual Resolution of (±)–ephedrine and Z–DL–Amino Acid Induced by Seeding Chiral Salt", Tetrahedron Letters No. 40, (1978), pp. 3813–3816.

Yang, Y–L., et al., "Mevinic Acids and Analogues: Preparation of a Key Chiral Intermediate", Tetrahedron Letters, (1982), vol. 23, No. 42, pp. 4305–4308.

Yoshino et al. Diabetes Research and Clinical Practice 2 (1986) 179–181.

*Pfizer Inc, et al. v. Ranbaxy Pharmaceuticals Limited, et al.,* 457 F. 3d 1284 (Fed. Cir. 2006) (Exhibit 1 to Preliminary Amendment in copending U.S. Appl. No. 11/653,830).

*Pfizer Inc, et al. v. Ranbaxy Pharmaceuticals Limited, et al.,* 405 F. Supp. 2d 495 (D. Del. 2005) (Exhibit 2 to Preliminary Amendment in copending U.S. Appl. No. 11/653,830).

"Pfizer's Proposed Findings of Fact", CA No. 03–209–JJF (Exhibit 3 to Preliminary Amendment in copending U.S. Appl. No. 11/653,830).

"Pfizer's Proposed Supplemental Findings of Fact", CA No. 03–209–JJF (Exhibit 4 to Preliminary Amendment in copending U.S. Appl. No. 11/653,830).
"Pfizer's Proposed Conclusions of Law", CA No. 93–209–JJF (Exhibit 5 to Preliminary Amendment in copending U.S. Appl. No. 11/653,830).
"Pfizer's Proposed Supplemental Conclusion of Law", CA No. 03–209–JJF (Exhibit 6 to Preliminary Amendment in copending U.S. Appl. No. 11/653,830).
"Opening Proposed Findings of Fact and Conclusions of Law of Defendants Ranbaxy Laboratories Limited and Ranbaxy Pharmaceuticals Inc.", CA No. 03–209–JJF (Exhibit 7 to Preliminary Amendment in copending U.S. Appl. No. 11/653,830).
"Petition for Panel Rehearing and Petition for Rehearing En Banc by Defendants–Appellants Ranbaxy Laboratories Limited and Ranbaxy Pharmaceuticals Inc." No. 2006–1179 (Exhibit 8 to Preliminary Amendment in copending U.S. Appl. No. 11/653,830).
"Plantiff–Appellee's Response to Petition for Rehearing and Rehearing En Banc", No. 2006–1179 (Exhibit 9 to Preliminary Amendment in copending U.S. Appl. No. 11/653,830).
"Order" denying Request for Panel Rehearing ad Rehearing En Banc (Exhibit 10 to Preliminary Amendment in copending U.S. Appl. No. 11/653,830).
"Pfizer's Post–Trial Opening Brief", CA No. 03–209–JJF (Exhibit 11 to Preliminary Amendmen in copending U.S. Appl. No. 11/653,830).
"Opening Post–Trial Brief of Defendants Ranbaxy Laboratories Limited and Ranbaxy Pharmaceuticals Inc.", CA No. 03–209–JJF (Exhibit 12 to Preliminary Amendment in copending U.S. Appl. No. 11/653,830).
"Pfizer's Corrected Post–Trial Reply Brief", CA No. 03–209–JJF (Exhibit 13 to Preliminary Amendment in copending U.S. Appl. No. 11/653,830).
"Defendant Ranbaxy Laboratories Limited's and Ranbaxy Pharmaceuticals Inc.'s Opposition Post–Trial Brief", CA No. 03–209–JJF (Exhibit 14 to Preliminary Amendment in copending U.S. Appl. No. 11/653,830).
Summaries of Non–United States Proceedings Involving Counterparts to U.S. Pat. No. 5,273,995, including: i) List of Countries (3 sheets); ii) Table of Foreign Lawsuits (5 sheets); and iii) Lipitor Canada Enantiomer Cases Document Schedules (28 sheets) (Exhibits 15, 15A and 15B in copending U.S. Appl. No. 11/653,830).
"Brief of Defendants–Appellants Ranbaxy Laboratories Limited and Ranbaxy Pharmaceuticals, Inc." No. 06–1179 (Exhibit 16 to Preliminary Amendment in copending U.S. Appl. No. 11/653,830).
"Brief of Plaintiffs–Appellees, Pfizer Inc." No. 06–1179 (Exhibit 17 to Preliminary Amendment in copending U.S. Appl. No. 11/653,830).
"Reply Brief of Defendants–Appellants Ranbaxy Laboratories Limited and Ranbaxy Pharmaceuticals, Inc." No. 06–1179 (Exhibit 18 to Preliminary Amendment in copending U.S. Appl. No. 11/653,830).
*Sanofi–Synthelabo et al. v. Apotex, Inc. et al.*, No. 06–1613 (Fed. Cir. Dec. 8, 2006) (Exhibit 20 to Preliminary Amendment in copending U.S. Appl. No. 11/653,830).
US 5,273,995 prosecution history, marked as Defendant's Trial Exhibit 139 in CA No. 022–209 (D. Del.) and comprising pages stamped RA0147320–RA014884 (Exhibit 22 to Preliminary Amendment in copending U.S. Appl. No. 11/653,830).

CA 1,330,441 file history which includes Canadian Patent Application No. 590,367 as filed Feb. 7, 1989.
CA 2,021,546 file history.
European Patent Application 87 107 847.3 file history.
European Patent Application 90 113 986.5 Claims (part of EP 0409281 file history C152).
European Patent Application 90 113 986.5 Claims as granted (part of EP 0409281 file history C152).
European Patent Application 90 113 986.5 (Jan 25, 2000 Communication) (part of EP 0409281 file history C152).
European Patent Application 90 113 986.5 Refusal (Sep. 5, 1998) (part of EP 0409281 file history C152).
European Patent Application 90 113 986.5 file history.
EP 0409281 file history.
US 4,618,893 file history.
US 5,003,080 file history.
"Petition for a Writ of Certiorani," *Ranbaxy Laboratories Limited et al. v. Pfizer Inc. et al.*, No. 06–1179, Jan. 22, 2007. (Exhibit 23 to Supplemental Communication in copending U.S. Appl. No. 11/653,830).
Pfizer Opposition to Ranbaxy Petition for Certiorani, Feb. 26, 2007. (Exhibit 24 to Supplemental Communication in copending U.S. Appl. No. 11/653,830).
Hall and Roush, *J. Org. Chem.*, 47: 4611–4621 (1982).
Roush and Gillis, *J. Org. chem.*, 47: 4825–4829 (1982).
Sit et al, *J. Med. Chem.*, 33:2982 (1990).
Amin et al., *J. Pharmacology* 46:13 (1993).
Underberg et al., *J. Pharm. Biomed Anal.* 8(8–12): 681–683 (1990).
Stinson, *Chemical and Engineering News*, 70(39): 46–79 (1992).
Stinson, *Chemical and Engineering News*, 71(39): 38–64 (1993).
Burlinson, *Tablets and Tabletting*, William Heinemann medical Books Ltd.: London, 1968.
Casy, A.F. Stereochemistry and Biological Activity. *Medicinal Chemistry*, Wiley: New York, 1970.
Rawlings, *Bentley's Textbook of Pharmaceutics*, $8^{th}$ Ed., Bailliere Tindall: London, 1977.
Seeman, P. Drug Receptors. Kalant H. et al. eds., *Principles of Medical Pharmacology*, $4^{th}$ Edition, University of Toronto Press: Toronto, 1985.
Lachman et al., Proformulation. *The Theory and Practice of Industrial Pharmacy*, $3^{rd}$ Edition, Lea & Febiger: Philadelphia, 1986.
Lieberman et al., eds. *Pharmaceutical Dosage Forms Tablets*, $2^{nd}$ Edition (vol. 1), Marcel Dekker: New York, 1989.
Gennaro, *Remington's Pharmaceutical Sciences*, $18^{th}$ Ed., Mack Printing Company: Easton, Pennsylvania, 1990.
Banker, Rhodes, eds., *Modern Pharmaceutics*, $3^{rd}$ Edition, Marcel Dekker, Inc.: New Yor, 1996.
Kibbe, A.H., ed., *Handbook of Pharmaceutical Excipients*, $3^{rd}$ Ed., Pharmaceutical Press: London, 2000.
The Merck Index, $10^{th}$ Edition (1983), entry 5949: *N–Methylglucamine*, pp. 870–871.
The Merck Index, $12^{th}$ Edition (1996), entry 897: *Atorvastatin*, p. 146.
Transcript of evidence given by Dr. Scallen in US trial of *Pfizer, Inc., et al. v. Ranbaxy Laboratories Limited et al.*, Court file No. 03–209–JJF, on Dec. 3, 2004.
Guideline for Submitting Supporting Documentation in Drug Applications for the Manufacture of Drug Substances, Feb. 1987.

Stein et al., The Lovastatin–Niacin Trial: Effects on Lipoproteins. *Arteriosclerosis and Thrombosis* 11: 1458a (1991).

Dujovne et al., The Lovastatin–Niacin Trial: Adverse Events. *Arteriosclerosis and Thrombosis* 11: 1458a (1991).

Frost, P.H. et al., Lipid Metabolism. In PA Fitzgerald, Ed., *Handbook of Clinical Endocrinology*, 2$^{nd}$ Edition, Appleton and Lange, 1991.

Frost, P.H. et al., Lovastatin–Niacin Comoparative Trial. *JACC* 19, 374A, 1992.

Lovastatin Study Groups I through IV. Lovastatin 5–year safety and efficacy study. *Arch. Intern. Med.* 153: 1079–1087 (1993).

Illingworth, D.R. et al., Comparative effects of lovastatin and niacin in primary hypercholesterolemia: A prospective trial. *Arch. Intern. Med.* 154: 1586–1595 (1994).

Stein, E.A. et al., Efficacy and tolerability of low–dose simvastatin and niacin, alone and in combination, in patients with combined hyperlipidemia: a prospective trial. J. *Cardiovasc. Pharmacol. Therapeut.* 1: 107–116 (1996).

Frost, P.H. et al., Rationale for use of non–high–density lipoprotein cholesterol rather than low–density lipoprotein cholesterol as a tool for lipoprotein cholesterol screening and assessment of risk and therapy. *Am. J. Cardiol.* 81: 26B–31B (1998).

Havel, R.J. et al., The role of non–high–density lipoprotein cholesterol in evaluation and treatment of lipid disorders. *J. Clin. Endocrinology and Metabolism* 85: 2105–2108 (2000).

The Cholesterol Myth, *Atlantic Monthly*, Sep. 1989.

National Cholesterol Education Program Guideline III (2004 Update).

Results of the National Cholesterol Education (NCEP) Program Evaluation Project Utilizing Novel E–Technology (Neptune) II Survey and Implications for Treatment under Recent NCEP Writing Group Recommendations.

Chaper 1—Selling to Everyone High Cholesterol. In Moynihan R. and Cassels A., *Selling Sickness*, Avalon Publishing Group: 2005, pp. 1–21.

Letter dated Dec. 2, 2005 from Taylor Wessing to L. Caswell attaching expert reports of Dr. Newton dated May 27, 2005 and Jun. 17, 2005 that were filed in *Ranbaxy (UK) Limited* v. *Warner–Lambert Company*, HC–04C 02167, and said reports.

Trial transcripts taken on Jul. 18 to 22, 2005 and Jul. 25, 2005 in *Ranbaxy (UK) Limited* v. *Warner–Lambert Company*, HC–04C 02167.

Warner–Lambert Company Notices of Application court files T–507–05, T–1128–05.

English translation of Austrian decisions invalidating Austrian Patent No. 207,896.

Lipitor advertising placed in the Canadian Medical Association Journal, from 1997 to 2005.

Consensus Conference. Lowering Blood Cholesterol to Prevent Heart Disease. *JAMA* 253: 1080–2086 (1985).

Report on the National Cholesterol Education Program Expert Panel on Detection, Evaluation, and Treatment of High Blood Cholesterol in Adults. The Expert Panel. *Arch. Intern. Med.* 148: 36–69 (1988).

Canadian Consensus Conference on Cholesterol. Final Report, Canadian Consensus Conference on the Prevention of Heart and Vascular Disease by Altering Serum Cholesterol and Serum Lipoprotein Factors. *CMAJ* 139: 111–63 (1988).

Frolich et al., Rationale for and Outline of the Recommendations of the Working Group of Hypercholesterolemia and Other Dyslipidemias: Interim Report. *Can. J. Cardiol.* 14 (supp. A): 17A–21A (1988).

Fodor et al., for the Working Group on Hypercholesterolemia and Other Dyslipidemias: Recommendations for the Management and Treatment of Dyslipidemia. CMAJ 162 (10): 1441–1447 (2000).

Fodor et al., Recommendations for the management of dyslipidemia and the prevention of cardiovascular disease: 2003 update. *CMAJ* 168 (9): 921–924 (2003).

NHLBI News Release May 15, 2001, http://www.nhlbi.nih.gov/new/press/01–05–15.htm.

Manuel et al., The 2003 Canadian Recommendations for Dyslipidemia Management: Revisions are Needed. *CMAJ* 172: 1027–1032 (2005).

Documents compiled by the World Health Organization's Department of Essential Drugs & Medicines Policy published as http://www.drugpromo.info/read–reviews.asp?id=4 and http://www.drugpromo.info/read–reviews.asp?id=5.

Wazana, A., *JAMA* 283(3): 373–380 (2000).

Brophy et al., Statin wars following coronary revascularization—Evidence based clinical practice? *Can. J. Cardiol.* 22(1): 54–58 (2006).

Havel et al., A multicenter study of mevinolin (lovastatin) in treatment of heterozygous familial hypercholesterolemia. *Annals Int. Med.* 107: 609 (1987).

Lovastatin Study Group III. A multicenter comparison of lovastatin and cholestyramine in the therapy of severe primary hypercholesterolemia. *JAMA* 260: 359 (1988).

Defendants' Trial Exhibit 3323, "Data Provided to Patent Office in '995 Specification and Data from Experiment 107," from *Pfizer, Inc et al.* v. *Ranbaxy Laboratories Limited, et al.*, US District Court, District of Delaware, 03–209–JJF.

Defendants' Trial Exhibit 3325 from *Pfizer, Inc et al.* v. *Ranbaxy Laboratories Limited, et al.*, US District Court, District of Delaware, 03–209–JJF.

Defendants' Trial Exhibit 3325A from *Pfizer, Inc et al.* v. *Ranbaxy Laboratories Limited, et al.*, US District Court, District of Delaware, 03–209–JJF.

Dietschy 1, CSI IC$_{50}$ values, from *Pfizer, Inc et al.* v. *Ranbaxy Laboratories Limited, et al.*, US District Court, District of Delaware, 03–209–JJF.

Dietschy 2, COR IC$_{50}$ values, from *Pfizer, Inc et al.* v. *Ranbaxy Laboratories Limited, et al.*, US District Court, District of Delaware, 03–209–JJF.

Dietschy 3, IC$_{50}$ values (nM) for head–to–head CSI and COR screens, from *Pfizer,, Inc et al.* v. *Ranbaxy Laboratories Limited, et al.*, US District Court, District of Delaware, 03–209–JJF.

Dietschy 4, AICS data, from *Pfizer, Inc et al.* v. *Ranbaxy Laboratories Limited, et al.*, US District Court, District of Delaware, 03–209–JJF.

Defendants' Trial Exhibit 319 from *Pfizer, Inc et al.* v. *Ranbaxy Laboratories Limited, et al.*, US District Court, District of Delaware, 03–209–JJF.

Defendants' Trial Exhibit 321 from *Pfizer, Inc et al.* v. *Ranbaxy Laboratories Limited, et al.*, US District Court, District of Delaware, 03–209–JJF.

Roth et al., Inhibitors of cholesterol biosynthesis. 3. Tetrahydro–4–hydroxy–6–[2–(1H–pyrrol–1–yl)ethyl]–2H–pyran–2–one inhibitors of HMG–CoA reductase. 2. Effects of introducing substituents at positions three and four of the pyrrole nucleus. *J. Med. Chem.* 34(1): 357–366 (Jan. 1991).

Warner–Lambert Pharmaceutical Research Report No. RR–740–02620, Acute Inhibition of Cholesterol Synthesis in the Rat by the Calcium Salts (Racemic and Chiral) of CI–971, dated May 31, 1989, identified as DTX 11 in *Pfizer, Inc et al.* v. *Ranbaxy Laboratories Limited, et al.,* US District Court, District of Delaware, 03–209–JJF.

Warner–Lambert/Parke–Davis memo to Oberkfell and Pieroni from Newton and Roth re: PD 134298–38A Product Profile A for HMG–Co–A Reductase Inhibitor, Jun. 1, 1989, identified as DTX 142 in *Pfizer, Inc et al.* v. *Ranbaxy Laboratories Limited, et al.,* US District Court, District of Delaware, 03–209–JJF.

Warner–Lambert/Parke–Davis Pharmaceutical Research Report RR–740–01682, CSI (Cholesterol Synthesis Inhibitors): A Rapid Screen for Inhibitors of Cholesterol Synthesis in Crude Microsomal Preparations from Rat Liver, dated May 3, 1985, identified as DTX 271 in *Pfizer, Inc et al.* v. *Ranbaxy Laboratories Limited, et al.,* US District Court, District of Delaware, 03–209–JJF.

Parke–Davis Memo re: Lead Compound Pharmacological Profile for CI–981 (PD 134298–38A) to Mr. H.F. Oberkfell and Mr. J. Peroni from Newton and Roth, dated Sep. 28, 1989, identified as DTX 4 in *Pfizer, Inc et al.* v. *Ranbaxy Laboratories Limited, et al.,* US District Court, District of Delaware, 03–209–JJF.

Chemist's Binder of Biological Data, identified as DTX 552, in *Pfizer, Inc et al.* v. *Ranbaxy Laboratories Limited, et al.,* US District Court, District of Delaware, 03–209–JJF.

CI–981 IND submitted to the FDA, identified as DTX 326 in *Pfizer, Inc et al.* v. *Ranbaxy Laboratories Limited, et al.,* US District Court, District of Delaware, 03–209–JJF.

SIT et al., Synthesis, Biological Profile, and Quantitative Structure Activity Relationship of a Series of Novel 3–Hydroxy–3–methylglutaryl Coenzyme A Reductase Inhibitors. *J. Med. Chem.* 33: 2982–2999 (1990).

Warner–Lambert/Parke–Davis Pharmaceutical Research Report No. RR967–01212, PD 123832 (Anti–Atherosclerosis)—Preformulation Summary, identified as DTX 28 in *Pfizer, Inc et al.* v. *Ranbaxy Laboratories Limited, et al.,* US District Court, District of Delaware, 03–209–JJF.

Warner–Lambert Report, "Atheroscleroris Drug Discovery Team Report," Dec. 12, 1989, referred to at paragraph 351 of *Ranbaxy Australia Pty Ltd* v. *Warner–Lambert Company LCC (No. 2),* [2006]FCA 1787.

Warner–Lambert internal report dated Dec. 15, 1987, summarizing results of CSI 107, referred to at paragraph 291 of *Ranbaxy Australia Pty Ltd* v. *Warner–Lambert Company LCC (No. 2),* [2006]FCA 1787.

Warner–Lambert internal memorandum dated Dec. 5, 1989, referred to at paragraph 341 of *Ranbaxy Australia Pty Ltd* v. *Warner–Lambert Company LCC (No. 2),* [2006]FCA 1787.

Forms IV. Lists for Atorvastatin Calcium in Canada.

US Orange Book entries for atorvastatin.

Letter of Aug. 19 1998 from US PTO to Francis J. Tinney regarding patent extension for Lipitor.

Letter of Nov. 7, 2005 from William Curatolo of Pfizer Global Research & Development and Stephen R Byrn of SSCI, Inc. to the Division of Dockets Management, food and Drug Administration, entitled Citizen Petition.

NOC listings for rosuvastatin, fluvastatin, pravastatin, lovastatin, atorvastatin, sinvastatin, cerivastatin.

Ranbaxy Reply in Support of Petition for Certiorari (Exhibit 25 to Supplemental Communication in copending U.S. Appl. No. 11/653,830).

Supreme Court decision denying Certiorari (Exhibit 26 to Supplemental Communicationin copending U.S. Appl. No. 11/653,830).

Ranbaxy's Apr. 12, 2007 ANDA Notice Letter (Exhibit 27 to Supplemental Communication in copending U.S. Appl. No. 11/653,830).

Pfizer Complaint (138 Delaware Action) (Exhibit 28 to Supplemental Communication in copending U.S. Appl. No. 11/653,830).

Ranbaxy Amended Answer and Counterclaims (138 Delaware Action) (Exhibit 29 to Supplemental Communication in copending U.S. Appl. No. 11/653,830).

Pfizer Reply to Ranbaxy's Amended Answer (138 Delaware Action) (Exhibit 30 to Supplemental Communication in copending U.S. Appl. No. 11/653,830).

Pfizer Briefs in Support of Motions to Dismiss (138 Delaware Action) (Exhibit 31 to Supplemental Communication in copending U.S. Appl. No. 11/653,830).

Ranbaxy Responses to Motions to Dismiss (138 Delaware Action) (Exhibit 32 to Supplemental Communication in copending U.S. Appl. No. 11/653,830).

Teva ANDA Notice Letter (Exhibit 33 to Supplemental Communication in copending U.S. Appl. No. 11/653,830).

KSR decision (Exhibit 34 to Supplemental Communication in copending U.S. Appl. No. 11/653,830).

Commissioner's Memorandum re: KSR decision (Exhibit 35 to Supplemental Communication in copending U.S. Appl. No. 11/653,830).

*Pfizer* v. *Apotex* decision (Exhibit 36 to Supplemental Communication in copending U.S. Appl. No. 11/653,830).

Order Denying Rehearing, and Dissents, in *Pfizer* v. *Apotex* decision (Exhibit 37 to Supplemental Communication in copending U.S. Appl. No. 11/653,830).

Danish decision, English translation (Exhibit 38 to Supplemental Communication in copending U.S. Appl. No. 11/653, 830).

Australian decision, *Ranbaxy Australia* v. *Warner–Lambert Co. LLC* (Exhibit 39 to Supplemental Communication in copending U.S. Appl. No. 11/653,830).

Canada decision, Docket T–507–05, dated Jan. 25, 2007 (Exhibit 40 to Supplemental Communication in copending U.S. Appl. No. 11/653,830).

*Pfizer Canada Inc.* v. *Canada (Minister of Health),* 2006 F.C. 1471 (Exhibit 41 to Supplemental Communication in copending U.S. Appl. No. 11/653,830).

EPO Technical Opinion (Exhibit 42 to Supplemental Communication in copending U.S. Appl. No. 11/653,830).

Pfizer Complaint (Exhibit 43 to Supplemental Communication in copending U.S. Appl. No. 11/653,830).

Ranbaxy's Jan. 24, 2007 ANDA Notice Letter (from "Amendment and Response to First Reissue Office Action" in copending U.S. Appl. No. 11/653,830).

Teva's Answer (with affirmative defenses) (from "Amendment and Response to First Reissue Office Action" in copending U.S. Appl. No. 11/653,830).

English Translation of Decision in Annulment Procedure in Spain (from "Amendment and Response to First Reissue Office Action" in copending U.S. Appl. No. 11/653,830).

English Translation of Decision in Invalidation Action in South Korea (from "Amendment and Response to First Reissue Office Action" in copending U.S. Appl. No. 11/653,830).

Order Granting Request for Ex Parte Reexamination of '893 Patent (from "Amendment and Response to First Reissue Office Action" in copending U.S. Appl. No. 11/653,830).

*Forest Laboratories, et al.* v. *Ivax Pharmaceuticals, Inc. and Cipla, Ltd.*, 2007 WL 2482122 (Fed. Cir. 2007) (from "Amendment and Response fo First Reissue Office Action" in copending U.S. Appl. No. 11/653,830).

*Aventis Pharma Deutschland GmbH and King Pharmaceuticals, Inc.* v. *Lupin, Ltd. and Lupin Pharmaceuticals, Inc.*, 2007 WL 2593791 (Fed. Cir. 2007) (from "Amendment and Response to First Reissue Office Action" in copending U.S. Appl. No. 11/653,830).

"Exhibit 53"—Record Support for the unexpected commercial and and medical success of Lipitor® as a result of its outstanding efficacy (from "Amendment and Response to First Reissue Office Action" in copending U.S. Appl. No. 11/653,830).

"Exhibit 54"—Record Support for: (1) Lipitor®'s satisfaction of a long–felt need in the medical community to provide patients with more effective statins to help them achieve their LDL goals; and (2) unsuccessful efforts by others to satisty the long–felt need in the medical community to provide patients with more effective statins (from "Amendment and Response to First Reissue Office Action" in copending U.S. Appl. No. 11/653,830).

"Exhibit 55"—Record Support for copying (e.g., by Ranbaxy) (from "Amendment and Response to First Reissue Office Action" in copending U.S. Appl. No. 11/653,830).

"Exhibit 56"—Declaration of James Thomas Sage ((from "Amendment and Response to First Reissue Office Action" in copending U.S. Appl. No. 11/653,830).

"Exhibit 57"—Outline of Appellant's Submissions (Appeal in Australian Proceedings) (from "Amendment and Response fo First Reissue Office Action" in copending U.S. Appl. No. 11/653,830).

"Exhibit 58"—Outline of Ranbaxy's Submissions (Appeal in Australian Proceedings) (from "Amendment and Response to First Reissue Office Action" in copending U.S. Appl. No. 11/653,830).

"Exhibit 59"—Outline of Appellant's Submissions in Reply (Appeal in Australian Proceedings) (from "Amendment and Response to First Reissue Office Action" in copending U.S. Appl. No. 11/653,830).

German Decision, Oct. 29, 2007 (English Translation).

Cobalt Pharmaceuticals, Paragraph IV Certification, Oct. 24, 2007.

*Takeda Chemical* v. *Alpha Pharm*, 06–1329 (Fed. Cir. 2007).

Request for Reexamination of US 4,681,893.

English Language version of DK 171588 B1 (Feb. 10, 1997).

Exhibit 60—Opinion of Delaware District Court—Ranbaxy Caduet® Case (Nov. 29, 2007).

J. W. Hubbard et al.; Clinical Biochemistry, vol. 19, pp. 107–112 (Apr. 1986).

Exhibit 15C—Updates and Corrections to Previous Exhibits 15, 15A and 15B.

Complaint, Civil Action No. 07–790, United States District Court for the District of Delaware, Dec. 6, 2007 (without exhibits).

Complaint, Civil Action No. 1:07–cv–12257, United States District Court for the District of Massachusetts, Dec. 7, 2007 (without exhibits).

\* cited by examiner

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–5 and 8–9 is confirmed.

Claims 6 and 7 were not reexamined.

\* \* \* \* \*